(12) United States Patent
Chang et al.

(10) Patent No.: US 8,048,440 B2
(45) Date of Patent: Nov. 1, 2011

(54) THERMOPLASTIC FLUOROPOLYMER-COATED MEDICAL DEVICES

(75) Inventors: James W. Chang, Flagstaff, AZ (US);
Robert L. Cleek, Flagstaff, AZ (US);
Edward H. Cully, Flagstaff, AZ (US);
Michael J. Vonesh, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 983 days.

(21) Appl. No.: 11/378,401

(22) Filed: Mar. 16, 2006

(65) Prior Publication Data

US 2006/0198866 A1    Sep. 7, 2006

Related U.S. Application Data

(62) Division of application No. 10/213,126, filed on Aug. 5, 2002, now abandoned.

(51) Int. Cl.
*A61F 2/82* (2006.01)
(52) U.S. Cl. ........................................... 424/423
(58) Field of Classification Search ........................ None
See application file for complete search history.

(56) References Cited

U.S. PATENT DOCUMENTS

| | | |
|---|---|---|
| 3,051,683 A | 8/1962 | Mallouk |
| 3,132,123 A | 5/1964 | Harris et al. |
| 3,467,638 A | 9/1969 | Pattison |
| 3,484,503 A | 12/1969 | Magner at al. |
| 3,635,926 A | 1/1972 | Gresham et at |
| 3,682,872 A | 8/1972 | Brizzolara at al. |
| 4,133,927 A | 1/1979 | Tomoda et al. |
| 4,138,426 A | 2/1979 | England |
| 4,194,041 A | 3/1980 | Gore et al. |
| 4,196,256 A | 4/1980 | Eddy et al. |
| 4,279,245 A | 7/1981 | Takagi et al. |
| 4,281,092 A | 7/1981 | Breazeale |
| 4,304,010 A | 12/1981 | Mano |

(Continued)

FOREIGN PATENT DOCUMENTS

CA    894898    3/1972

(Continued)

OTHER PUBLICATIONS

Barney AL et al. A High-Performance Fluorocarbon Elastomer. Journal of Polymer Science 1970; 8:1091-1098.

(Continued)

*Primary Examiner* — Carlos Azpuru
(74) *Attorney, Agent, or Firm* — Wayne D. House

(57) ABSTRACT

A medical device provided with at least a partial surface coating of a thermoplastic copolymer of tetrafluoroethylene and perfluoroalkylvinylether that is free of cross-linking monomers and curing agents. The fluoropolymer coating is preferably an amorphous thermoplastic, is highly inert and biocompatible, has elastomeric characteristics that provide desirable mechanical properties such as good flexibility and durability. These characteristics allow the coating to be considered "functionally transparent" because it withstands mechanical deformations required for the assembly, deployment, expansion, and placement of medical devices, without any adverse effect on the mechanical and biological functionality of the coated device. Further, its inertness, derived from the perfluorocarbon structure, contributes to its functionally transparent nature. The coating can be provided with various liquid or solid additives, can be loaded with large quantities of additives including a wide range of therapeutic agents, and has excellent drug elution characteristics when elutable additives are used. The desirable mechanical characteristics are surprising given the absence of cross-linking monomers and curing agents that would otherwise render such materials inadequately biocompatible. The perfluoroalkylvinylether may be perfluoromethylvinylether, perfluoroethylvinylether or perfluoropropylvinylether.

13 Claims, 21 Drawing Sheets

U.S. PATENT DOCUMENTS

| | | | |
|---|---|---|---|
| 4,316,836 A | 2/1982 | Aufdermarsh, Jr. |
| 4,380,618 A | 4/1983 | Khan et al. |
| 4,387,168 A | 6/1983 | Morita |
| 4,394,489 A | 7/1983 | Aufdermarsh |
| 4,413,094 A | 11/1983 | Aufdermarsh, Jr. |
| 4,443,511 A | 4/1984 | Worden et al. |
| RE31,618 E | 7/1984 | Mano et al. |
| 4,487,903 A | 12/1984 | Tatemoto et al. |
| 4,499,249 A | 2/1985 | Nakagawa et al. |
| 4,520,170 A | 5/1985 | Kitto |
| 4,525,539 A | 6/1985 | Feiring |
| 4,529,784 A | 7/1985 | Finlay |
| 4,576,869 A | 3/1986 | Malhotra |
| 4,600,651 A | 7/1986 | Aufdermarsh et al. |
| 4,619,641 A | 10/1986 | Schanzer |
| 4,670,328 A | 6/1987 | Kawachi et al. |
| 4,692,369 A | 9/1987 | Nomi |
| 4,713,418 A | 12/1987 | Logothetis et al. |
| 4,764,560 A | 8/1988 | Mitchell |
| 4,816,339 A | 3/1989 | Tu et al. |
| 4,859,836 A | 8/1989 | Lunk et al. |
| 4,864,006 A | 9/1989 | Giannetti et al. |
| 4,875,468 A | 10/1989 | Krauter et al. |
| 4,882,113 A | 11/1989 | Tu et al. |
| 4,891,407 A | 1/1990 | Mitchell |
| 4,897,457 A | 1/1990 | Nakamura et al. |
| 4,904,726 A | 2/1990 | Morgan et al. |
| 4,910,276 A | 3/1990 | Nakamura et al. |
| 4,935,467 A | 6/1990 | Cheng et al. |
| 4,945,125 A | 7/1990 | Dillon et al. |
| 4,955,899 A | 9/1990 | Dell Corna et al. |
| 4,982,009 A | 1/1991 | Hung |
| 4,983,680 A | 1/1991 | Ojakaar |
| 5,001,278 A | 3/1991 | Oka et al. |
| 5,059,720 A | 10/1991 | Hung |
| 5,061,276 A | 10/1991 | Tu et al. |
| 5,071,609 A | 12/1991 | Tu et al. |
| 5,100,422 A | 3/1992 | Berguer et al. |
| 5,104,400 A | 4/1992 | Berguer et al. |
| 5,122,441 A | 6/1992 | Lawton et al. |
| 5,152,782 A | 10/1992 | Kowligi et al. |
| 5,179,167 A | 1/1993 | Ishiwari et al. |
| 5,180,803 A | 1/1993 | Gibbard |
| 5,192,310 A | 3/1993 | Herweck et al. |
| 5,217,797 A | 6/1993 | Knox et al. |
| 5,219,904 A | 6/1993 | Abe |
| 5,256,747 A | 10/1993 | Ojakaar et al. |
| 5,266,639 A | 11/1993 | Chapman, Jr. et al. |
| 5,268,405 A | 12/1993 | Ojakaar et al. |
| 5,290,271 A | 3/1994 | Jernberg |
| 5,310,838 A | 5/1994 | Hung et al. |
| 5,320,888 A | 6/1994 | Stevens |
| 5,328,946 A | 7/1994 | Tuminello et al. |
| 5,364,699 A | 11/1994 | Hollenbaugh et al. |
| 5,376,441 A | 12/1994 | Wu et al. |
| 5,383,928 A | 1/1995 | Scott et al. |
| 5,385,694 A | 1/1995 | Wu et al. |
| 5,397,829 A | 3/1995 | Morgan et al. |
| 5,422,159 A | 6/1995 | Fagan |
| 5,460,872 A | 10/1995 | Wu et al. |
| 5,461,107 A | 10/1995 | Amin et al. |
| 5,461,129 A | 10/1995 | Kurihara et al. |
| 5,463,006 A | 10/1995 | Abusleme |
| 5,464,904 A | 11/1995 | Chapman, Jr. et al. |
| 5,466,252 A | 11/1995 | Soukup et al. |
| 5,523,346 A | 6/1996 | Wu |
| 5,529,820 A | 6/1996 | Nomi et al. |
| 5,539,047 A | 7/1996 | Wu et al. |
| 5,539,072 A | 7/1996 | Wu |
| 5,543,217 A | 8/1996 | Morgan |
| 5,552,219 A | 9/1996 | Vita et al. |
| 5,554,680 A | 9/1996 | Ojakaar |
| 5,560,986 A | 10/1996 | Mortimer, Jr. |
| 5,565,512 A | 10/1996 | Saito et al. |
| 5,589,557 A | 12/1996 | Navarrini et al. |
| 5,677,366 A | 10/1997 | Wu |
| 5,696,189 A | 12/1997 | Legare |
| 5,702,441 A | 12/1997 | Zhou |
| 5,708,044 A | 1/1998 | Branca |
| 5,741,323 A | 4/1998 | Pathak |
| 5,776,184 A | 7/1998 | Tuch |
| 5,824,049 A | 10/1998 | Ragheb et al. |
| 5,837,008 A | 11/1998 | Berg et al. |
| 5,851,217 A | 12/1998 | Wolff et al. |
| 5,851,231 A | 12/1998 | Wolff et al. |
| 5,877,264 A | 3/1999 | Logothetis et al. |
| 5,919,878 A | 7/1999 | Brothers et al. |
| 5,973,091 A | 10/1999 | Schmiegel |
| 5,986,012 A | 11/1999 | Legare et al. |
| 6,099,562 A | 8/2000 | Ding et al. |
| 6,120,536 A | 9/2000 | Ding et al. |
| 6,140,437 A | 10/2000 | Kitaichi et al. |
| 6,211,319 B1 | 4/2001 | Schmiegel |
| 6,248,823 B1 | 6/2001 | Hrivnak et al. |
| 6,299,604 B1 | 10/2001 | Ragheb et al. |
| 6,306,166 B1 | 10/2001 | Barry et al. |
| 6,306,176 B1 | 10/2001 | Whitbourne |
| 6,309,380 B1 | 10/2001 | Larson et al. |
| 6,322,847 B1 | 11/2001 | Zhong et al. |
| 6,329,469 B1 | 12/2001 | Bowers et al. |
| 6,358,556 B1 | 3/2002 | Ding et al. |
| 6,364,903 B2 | 4/2002 | Tseng et al. |
| 6,419,692 B1 | 7/2002 | Yang et al. |
| 6,426,386 B2 | 7/2002 | Lee et al. |
| 6,451,373 B1 | 9/2002 | Hossainy et al. |
| 6,471,980 B2 | 10/2002 | Sirhan et al. |
| 6,485,514 B1 | 11/2002 | Wrenn, Jr. |
| 6,503,556 B2 | 1/2003 | Harish et al. |
| 6,531,559 B1 | 3/2003 | Smith et al. |
| 6,939,593 B2 | 9/2005 | Wang |
| 7,049,380 B1 | 5/2006 | Chang et al. |
| 2002/0168394 A1 | 11/2002 | Hossainy et al. |
| 2003/0017190 A1 | 1/2003 | Sirhan et al. |
| 2005/0125054 A1 | 6/2005 | Bhat et al. |

FOREIGN PATENT DOCUMENTS

| | | |
|---|---|---|
| DE | 4131746 | 9/1991 |
| DE | 100 27 855 | 12/2001 |
| EP | 0 293 090 | 4/1987 |
| EP | 0 256 748 | 2/1988 |
| EP | 0 352 972 | 1/1990 |
| EP | 0 269 449 | 2/1994 |
| EP | 0 679 373 | 4/1994 |
| EP | 0 633 032 | 1/1995 |
| EP | 0 716 834 | 6/1996 |
| EP | 0 818 489 | 1/1998 |
| EP | 0 950 386 | 4/1998 |
| EP | 0 953 320 | 11/1999 |
| EP | 1 192 957 | 9/2000 |
| EP | 1 273 314 | 7/2001 |
| JP | 54-74514 | 11/1977 |
| JP | 59-25725 | 8/1982 |
| JP | 08-168521 | 7/1996 |
| JP | 09-019500 | 1/1997 |
| JP | 09-173438 | 7/1997 |
| JP | 10-323386 | 12/1998 |
| JP | 2002-293953 | 10/2002 |
| RU | 2071479 | 1/1997 |
| WO | 91/18930 | 12/1991 |
| WO | 94/02185 | 2/1994 |
| WO | 94/24625 | 9/1996 |
| WO | 96/32907 | 10/1996 |
| WO | 99/41313 | 2/1998 |
| WO | 98/11146 | 3/1998 |
| WO | 98/57680 | 12/1998 |
| WO | 00/08071 | 2/2000 |
| WO | 00/32255 | 9/2000 |
| WO | 00/59963 | 10/2000 |
| WO | 02/26139 | 4/2002 |
| WO | 02/26271 | 4/2002 |
| WO | 02/26280 | 4/2002 |
| WO | 02/26281 | 4/2002 |
| WO | 03/018079 | 3/2003 |
| WO | 03/037397 | 5/2003 |
| WO | 2004/026359 | 4/2004 |

OTHER PUBLICATIONS

Barney AL et al. Vulcanizate Properties From a New Perfluoroelastomer. Rubber Chemistry and Technology 1971; 44(3):660-667.
Berman M et al. The use of GORE-TEX® e-PTFE Bonded to Silicone Rubber as an Alloplastic Implant Material. Laryngoscope 1986; 96(5):480-483.
Carlson, PD et al. Fluoropolymers, Organic vol. A 11: 393, 423-427.
DuPont Dow elastomers-Kalrez®. Copyright 1999 DuPont Dow Elastomers.
Hyflon®PFA technical brochure. Aussimont USA, Inc., 1991.
Hyflon@MFA Perfluoropolymer technical brochure. Aussimont USA, Inc., May 1998.
Hyflon®MFA 6010X PFA 7010 powder coating manual. Aussimont USA, Inc., Oct. 1998.
Kalb GH et al. A New Engineering Material for Advanced Design Concepts. Applied Polymer Symposium 1973; 22:127-142.
Kalb GH et al. Terpolymers of Tetrafluoroethylene, Perfluoro (Methyl Vinyl Ether) and Certain Cure Site Monomers. Polymer Preprints 1972; 13(1):190-492.
Kalb GH et al. Terpolymers of Tetrafluoroethylene, Perfluoro (Methyl Vinyl Ether) and Certain Cure Site Monomers. In: *Polymerization Reactions and New Polymers*, ed. Platzner, Norbert A.J. Publised by American Chemical Societh 11973; 13-26.
Kalrez® perfluoroelastomer parts. Physical Properties and Compound Comparisons. Copyright 1996, 1998 DuPont Dow Elastomers.
Kalrez® perfluoroelastomer parts. Compound Selection Guide. Copyright 1997 DuPont Dow Elastomers.
Kalrez® makes seals you can bank on. Copyright 1998 DuPont Dow Elastomers.
Legere JM et al. Characterization of Elemental Extractables in Perfluoroelastomer and Fluoroelastomer Sealing Materials. Microcontamination Conference Proceedings 1993; 36-46.
Logothetis AL Chemistry of Fluorocarbon Elastomers. Prog. Polym. Sci. 1989; 14:251-296.
Logothetis AL Perfluoroelastomers and Their Functionalization. In: *Macromolecular Design of Polymeric Materials*, ed. Hatada K, Kitayama T. Vogl O. New York: Marcel Dekker, Inc. 1997; 447-455.
Marshall JB Kalrez©-Type Perfluoroelastomers—Synthesis, Properties and applications. In: *Modern Fluoropolymers*. ed. Scheirs J. New York 1997; 349-358.
Vita G and Pozzoli M. MFA: A New Perfluoropolymer for Wire & Cable Applications. International Wire and Cable Symposium Proceedings 1995; pp. 809-816.

20X mag 260X mag

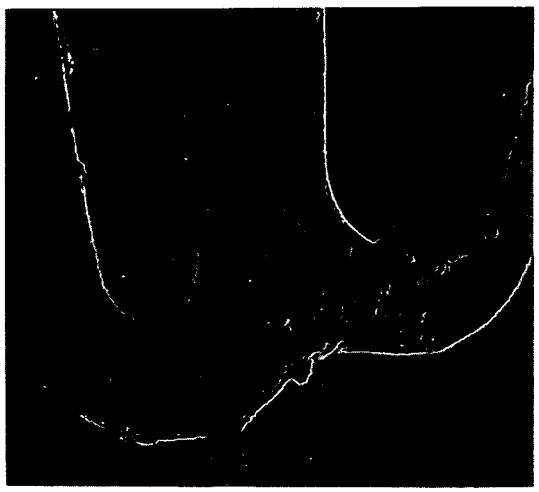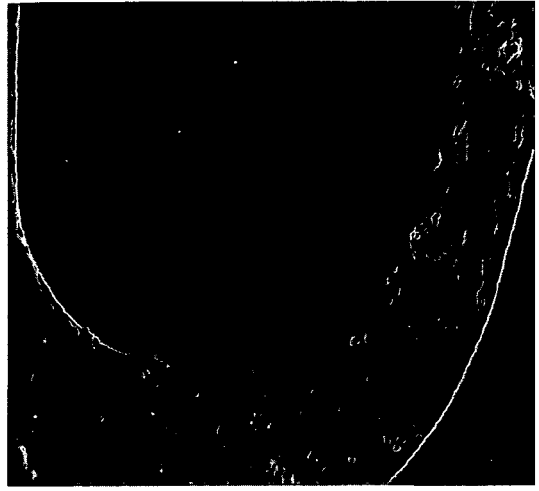
Fig. 10A
100X mag
Fig. 10B
200X mag 15X mag 15X mag 15X mag 30X mag 15X mag 30X mag 10X mag 30X mag 30X mag 30X mag 15X mag 15 X mag 20X mag 25X mag 30X mag

THERMOPLASTIC FLUOROPOLYMER-COATED MEDICAL DEVICES

CROSS REFERENCE TO RELATED APPLICATIONS

This application is a divisional of application Ser. No. 10/213,126 filed Aug. 5, 2002 now abandoned.

FIELD OF THE INVENTION

The present invention relates to the field of medical devices provided with at least a partial surface coating of polymer.

BACKGROUND OF THE INVENTION

Surgical interventions often involve the implantation of a medical device, typically manufactured from polymeric and/or metallic materials, that is intended to provide a mechanical repair of a medical malady. While providing necessary and often life saving benefits, the implanted metal or polymer material may also produce some type of complication. Some of the more common complications include acute thrombosis; increased risk of infection immediately post procedure and/or chronically; fibrous encapsulation of the device resulting from a foreign body response and inflammation; and vascular proliferative disease resulting in an excessive, inflammatory, fibroproliferative response to injury.

In some cases therapeutic agents are administered to ameliorate complications arising from the medical implant and the disease being treated. Most often these are administered orally or through injection and result in systemic delivery. Ideally therapeutic agents would be released locally in a controlled fashion from an implant to maximize the effectiveness of the agent at the desired site without causing severe systemic side effects. A combination device, or product, that provides for local drug delivery and a mechanical solution to the medical malady may result in clinical outcomes not possible otherwise. One approach to achieving this combination is through the use of coatings applied to the surfaces of medical devices, implantable for short or long terms, wherein the coating may optionally contain therapeutic agents elutable from the coating.

Many systemic pharmacological approaches to reducing restenosis have been proposed including the use of various agents such as anticoagulants, antiplatelet agents, metalloprotease inhibitors, antiproliferative agents and anti-inflammatory agents. Many of these compounds have demonstrated some level of positive effect in animal models of restenosis. Unfortunately, the clinical application of these compounds has shown no positive indications. This ineffectiveness may be largely attributed to the inability of systemic delivery to provide effective drug concentrations at the desired site. The dose and manner in which these compounds are administered is suboptimal, necessitating the development of new delivery modalities, technologies, and materials to accomplish effective localized delivery. Furthermore, potentially useful but toxic agents that would otherwise not be considered because of problematic systemic concentration from injections or oral dosage forms, could be used in combination products with an effective localized delivery system.

While there is large potential for combination products that provide therapeutic delivery with medical devices, development has been slow. For example, the use of localized stent-based drug delivery to reduce restenosis has only recently been demonstrated in limited clinical trials. Many of the drugs being proposed for use in these combination devices have existed for many years. Paclitaxol is a prime example as it has long been used as a cancer therapy, and its effects on vascular cells have been known for some years. The slow emergence of these combination products then appears to be due to the lack of adequate materials to combine the drug and device into one medical embodiment that meets all the needs for clinical applications. Each combination product requires a suitable drug, a robust medical device, and a means to combine these two elements together in a single entity. Most often a polymer coating has been proposed as the material to combine the drug and device into a single entity. Unfortunately, many of the materials currently available have numerous shortcomings.

There is a need for biocompatible materials that can adequately retain an efficacious dose, provide for prolonged drug release, and be incorporated into the mechanical device, in the simplest possible fashion, without compromising the device functionality. Moreover, the material would truly be exemplary if it provided more benefits to the combination product than functioning solely as a matrix for the release of a therapeutic agent. Preferably, this can be accomplished without the addition of still another component, such as an adhesive material or primer coatings, or without requiring surface modification of the medical device, but rather with the polymer material itself serving as a biocompatible adhesive with or without additives.

The utilization of biodegradable materials for drug delivery such as alpha hydroxy esters is well known. These compounds have glassy or rigid amorphous states that do not meet the flexibility requirements of combination implantable device. These materials have poor adhesive properties, particularly with regard to common materials used to manufacture medical devices such as various metals and polymers such as polytetrafluoroethylene (PTFE). The biodegradable nature of these materials requires judicious use so as not to create fragmentation of the material and possibly the device as they degrade.

Silicones are among the most widely used synthetic polymers that are intended to be non-biodegradable and are found in a variety of medical applications. They are sometimes used as a matrix material for elution of therapeutic agents, and as an elastomer they offer a good degree of flexibility. See, for example, U.S. Pat. No. 6,358,556 to Ding et al. Silicones consist of at least three components: an elastomer, silica reinforcing agent, and a volatile inhibitor to stop cross-linking. However, silicones have poor bonding strengths to many medical device substrate materials, and poor long-term in vivo tensile strength. They are less biocompatible than most fluoropolymers. Silicones absorb lipids and proteins over time, have a tendency to generate particulate debris over time, and exhibit poor abrasion resistance. Curatives in the vulcanized polymer can be problematic in that they may react with additive. Other problems are known to include cracking, swelling (generally due to lipid or protein absorption), tear propagation and poor adhesion. These problems are exacerbated by the use of additives.

Various fluoropolymer materials have been proposed as drug delivery material; see, for example, EP 950386 to Llanos et al. which suggests a list of materials including PTFE. While PTFE is particularly inert and highly biocompatible, it is not elastomeric and is limited in elution capability if not used in its porous expanded form (ePTFE). Drugs are typically eluted from the interconnected void spaces of ePTFE rather than by molecular diffusion from within the polymer matrix; see, for example, U.S. Pat. No. 5,290,271 to Jemberg. EP 1192957 to Llanos et al., proposes other fluoropolymer materials comprising a first monomer chosen from the group consisting of vinylidene fluoride and a second monomer that is different from the first monomer. These materials are relatively non-durable according to examples that describe cracking of the matrix during device expansion. Likewise, these particular materials are limited in their drug loading and drug elution capabilities. The ability to bond to a variety of other materials without requisite primer coating or surface treatment of the substrate, the ability to function as an integral component of a coated medical device (without adverse effect on the device function), and the ability to aid in the manufacturing of a wide range of combination products has not been shown

SUMMARY OF THE INVENTION

The present invention provides a coating for a medical device that can also act as a vehicle for delivery of therapeutic agents. The coating comprises a fluoropolymer that is highly inert and biocompatible, has elastomeric characteristics that provide desirable mechanical properties such as good flexibility and durability, can be loaded with additives (such as therapeutic agents) either in solid or liquid form, and as such has excellent drug elution characteristics.

The coating material is a thermoplastic copolymer of tetrafluoroethylene (TFE) and perfluoroalkylvinylether (PAVE) that is free of cross linking monomers and curing agents. The coating material is preferably an amorphous thermoplastic. The perfluoroakylvinylether may be perfluoromethylvinylether (PMVE), perfluoroethylvinylether (PEVE) or perfluoropropylvinylether (PPVE). The desirable mechanical characteristics are surprising given the absence of cross-linking monomers, curing agents and processing aids or fillers that would otherwise typically render such materials inadequately biocompatible. The use of the coating on a medical device results in a new, composite device that combines the attributes of the inert, durable coating with the utility of the device itself and, in addition, provides a vehicle for delivery of a therapeutic agent.

The coating material is considered "functionally transparent" for most medical device coating applications. This means that the coating accomplishes its intended purposes without adverse effect on the intended function of the coated medical device. The coating material provides this unique feature in its ability to withstand mechanical deformations required for the assembly, deployment, expansion, and placement of medical devices, to such an extent that the user of such devices does not realize that the material is present. The coating is functionally transparent to the coated medical device even while containing additives and providing for controlled release of therapeutic additives, if desired. The coating material has good adhesive properties, such that it does not require a primer or other surface treatment of the substrate to be coated, and thus, can allow for thin coatings with or without additives that can also be used to bond components of the device together. Because of its perfluorocarbon nature, it has substantially no adverse effect on the in-vivo function of the device. This inertness within a living body contributes to its functionally transparent character. It can be used with a wide range of additives while being able to accommodate high levels of loading of such additives.

A medical device is hereby defined as any device used in the cure, mitigation, treatment, or prevention of disease, in man or other animals, or intended to affect the structure or any function of the body of man or other animals. Medical devices are typically used in contact with any body fluids or body tissues of man or other animals. Implantable medical devices are those devices that are inserted into living bodies for appreciable periods. More specifically, long term implants are defined as items implanted for more than 30 days while devices inserted into living bodies for lesser periods are considered to be short term implantable devices.

For purposes of the present invention, additives are considered herein to be any additional materials added to the TFE/PAVE copolymer for any reason, regardless of form. They may therefore be in the form of liquids or solids; they may represent solutions (including colloidal suspensions), mixtures, blends, particulates, etc.

The term "amorphous" is used herein to define a polymer that is substantially non-crystalline, and in which the molecular chains exist in the random coil conformation, with little or no regularity of structure. The copolymer has sufficient amounts of PAVE in the molecular chains to substantially disrupt the crystallinity of the resulting fluoropolymer. Crystallinity can be detected by thermal/calorimetric techniques which measure the latent heat of the melting/freezing transitions. One convenient method of detection known to those of skill in the art is by Differential Scanning Calorimetry (DSC). The heat of fusion calculated from any endotherm detected in a DSC scan for the as-polymerized copolymer is no more than about 3J/g, and preferably no more than about 1J/g. The scan rate should be set at 10° C. per minute over a temperature range beginning at 60° C. and ending at 400° C.

The term "thermoplastic" is used herein to define a polymer that will repeatedly soften when exposed to heat and return to its original condition when cooled to room temperature. Such a polymer can be made to soften, flow or take on new shapes, without significant degradation or alteration of the polymer's original condition, by the application of heat or heat and pressure. A thermoplastic is accordingly a polymer in which the molecular chains are held together by the secondary van der Waals bonds; when enough thermal energy is applied, the chains break free from one another and the material will flow and melt.

In contrast to a thermoplastic polymer, a "thermoset" polymer is hereby defined as a polymer that solidifies or "sets" irreversibly when cured. Thermoset polymers have a three-dimensional network structure which prevents chains from being freed at higher temperatures. They will typically burn instead of melt.

A determination of whether a polymer is a "thermoplastic" polymer within the meaning of the present invention can be made by slowly elevating the temperature of a slightly tensioned specimen and watching for deformation. If the polymer can be made to repeatedly soften, flow, or take on a new shape, without significant degradation or alteration of the polymer's original chemical condition, then the polymer is considered to be a thermoplastic. If only small amounts of material are available it may be necessary to use a hot stage microscope for this determination.

A variety of different types of medical devices can benefit from the inventive coatings. Stents, including both balloon expandable and self-expanding stents, are particularly improved by coating with the fluoropolymer. The change of overall dimensions of the stent is accommodated by the good flexibility and durability of the coating material. Coated stents of the present invention can be used for applications in vascular and non-vascular body conduits such as biliary, hepatic or esophageal. The flexibility and adhesion of the coating substantially reduces or eliminates risk of cracking during stent expansion. The durability of the coating reduces risk of damage to the coating by a stent delivery catheter or by the luminal surface of the body conduit into which it is inserted. This is of particular utility during single balloon procedures when the balloon is inserted into a lesion together with a stent, wherein the balloon simultaneously expands the stent and forcibly opens up the stenosis at the device deployment site.

Stent-grafts, that is, stents that are provided with a covering, often of a tubular graft material, that covers some or all of the otherwise open interstices of a deployed stent, can also be provided with a coating over the surfaces of the stent and/or the surfaces of the graft material with beneficial results. The tubular graft material is most typically PTFE, PET or polyurethane. The coating may be used as an adhesive to join the graft covering to the stent. Likewise, it may be desirable to cover surfaces selectively so that only some surfaces are covered, or some surfaces are only partially covered. Further, the coating material itself may be used in the form of a thin film as the graft covering material. The film may be applied in the form of thin sheets, tapes or tubes to the desired surface of a stent to create a stent-graft, covering the stent elements and the interstices between adjacent elements. Alternatively, a stent may be dipped into the coating to achieve a covering that covers the stent elements and spans the stent interstices, thereby resulting in a stent-graft The coating may be used with or without additives. For example, the coating may be used beneficially without an additive by covering a less biocompatible material, in effect passivating the less biocompatible material.

Because both stent elements and graft coverings for stent-grafts may be beneficially covered by the inventive coating (with or without additives) without significant adverse affect on device profile (for thin coatings) and without adverse effects on the coating such as cracking during device deployment, the coating is deemed particularly useful for all bendable elements of medical devices including both stent elements and graft coverings for stent-grafts. Bendable elements are considered to be those elements of a medical device that undergo bending during insertion into or use with a body. Expandable endoluminal elements are considered to be those portions of an expandable device such as a stent that undergo a change of dimension during the course of the expansion of the device, from its initial shape appropriate for insertion into a body and transfer to a desired site, to its deployed size at the desired site.

There may be multiple such elements within a single device that, while integral to the device, undergo appreciably more change than adjacent portions of the device. Conversely, the entire device may constitute a single such element if the change of shape is accomplished relatively uniformly over virtually the entire device, as, for example, with many self-expanding stents.

Devices such as vascular grafts, venous valves, heart valves and heart valve leaflets, left ventricular assist devices, ocular implants including lenses and corneal implants, device introducers, access ports, topically-applied devices (e.g., wound dressings and transdermal patches), embolic filters, embolic particles, catheters, device delivery components, catheter balloons, guidewires, occluders, implantable electrical leads and devices, implantable patches including vascular and hernia patches, sutures and other surgical fasteners, and orthopedic implants can be beneficially coated. Catheter balloons for stent delivery can be beneficially coated to improve their ability to retain a stent during insertion of a stent delivery system into a body conduit, substantially reducing any risk of loss or misplacement of a stent during the insertion process due to the stent having inadvertently moved with respect to the balloon surface. This risk can be considerable when it is attempted to insert a catheter balloon and stent into a restrictive vascular lesion. Vascular grafts can be provided as tubular grafts or as sheet grafts for the repair of only a portion of the circumference of a blood vessel. This list is intended only to be representative of the types of medical devices that may be improved by the present invention, and consequently is not limiting. Further, the coating (with or without an additive) may be used as an adhesive between different components of a medical device.

The medical devices can be coated by a variety of known processes including spraying, dip-coating, powder coating, dispersion coating, lamination to other substrates, extrusion, molding, compression molding, or any other suitable means. It can be applied as very thin coatings, even when loaded with additive materials, and as such it enables medical devices to be made with minimal effect on the thickness and profile of the devices. The coating material adheres well to a variety of substrates including various metals (e.g., stainless steels and nitinols) and to various polymers (e.g., ePTFE). It does not require special preparation of the substrate surface, additional bonding agents, or high temperature processing.

Because the coating material adheres well and because it has an elastomeric character, it is effective for use on stents and stent-grafts. The coating is not adversely affected by the stent deployment process involving expansion of the stent diameter from its small, compacted diameter at which it was inserted into the vasculature, up to its larger diameter following deployment and expansion. The coating does not crack or otherwise disrupt during this expansion process, which may involve plastic deformation of the metallic stent elements. Any elutable therapeutic agent contained in the coating can thus be expected to follow its intended release rate because of the robust and durable character of the coating, minimizing risk of cracking or loss of adhesion. The coating may be employed in the manufacture of medical devices as a drug-eluting adhesive. The coating material is self-adhesive, meaning that additional layers of the coating will adhere well to previously applied layers.

When used with solvents such as FC-75 fluorinated solvent (3M Fluorinert, 3M Specialty Chemicals Division, St. Paul, Minn.), the inventive coating material can be a practical, low temperature adhesive. It is generally preferable to use solvents of this type that typically do not dissolve or chemically react with most additives. A uniform coating of a heterogeneous mixture of a drug and the copolymer is possible with the present invention. This allows for coexistence of drug-loaded regions adjacent to drug-free regions in a pattern design that most efficiently delivers a drug (or other therapeutic agent) in a localized, strategic fashion. Thus, one common solvent and polymer are used to easily create polymer-drug regions in contact with polymer-coated regions that do not contain drugs.

The coating may be applied over any or all surfaces of a medical device. The coating can be provided over the entire surface area of a medical device in a fully continuous fashion whereby none of the original surface of the device remains exposed. Alternatively, only some surfaces may be covered or some surfaces may only be partially covered. The coating may be provided in discontinuous fashion such that it is interrupted at desired portions of a surface, for example, the coating may be provided as a dot-matrix pattern on a desired surface.

The coating can be provided as a film, in the form of thin sheets or tubes, in which form it can be used for numerous applications. For example, the film can be used as the covering material over various devices (including, as previously mentioned, a stent to create a stent-graft). It may be used as a stand-alone biological barrier material, for example, to separate different types of living tissues during healing. It can be applied over other substrates and subsequently bonded to the substrate by the use of heat or by the use of more of the coating polymer in a liquid form as an adhesive. Films can be made with conventional methods including extrusion and solvent casting. They can be separately made for subsequent application to the surface of a device, or alternatively can be provided by techniques such as dip-coating directly over the surfaces of various devices (such as, for example, guidewires and stents).

The coating can be provided over porous substrates in order to reduce their porosity and/or permeability, including to an extent that the porous substrate is rendered non-porous across opposing surfaces of a device made from the porous substrate.

Likewise, the coating can be provided in porous forms. The copolymer material may be rendered porous by methods such as the inclusion of foaming agents, dissolving impregnated particles or by forcing gasses or supercritical fluids through the thermoplastic coating.

The coating material can be provided with a wide variety of additives including a variety of therapeutic agents. Depending on the type of additive used (particularly with regard to the inertness of the additive), the additive can remain stable and resident with the coating material (e.g., radiopaque additives), or alternatively an additive can be provided to allow for its elution over a specific period. Solid or liquid additives may be used with the coating material at the time of coating the medical device surface. While smaller particle sizes are preferred for particulate additives, the coating material can accommodate larger particle sizes with minimal effect on the mechanical properties of the coating.

Additives, including those that are intended to elute, may be provided in relatively high weight percent amounts, such as about 1, 2, 5, 10, 20, 30, 40, 50, 60, or 70 weight percent, or more. Elutable additives may be provided with an additional capping layer of the coating polymer in order to reduce the rate of elution and extend the time of elution. The capping layer may be provided over another filled layer of the coating, or alternatively may be applied directly over a layer of the additive material itself in some instances. Likewise, a capping layer may contain an additive which is different from an additive contained beneath the capping layer. The release kinetics may be varied in other ways, such as, for example for particulate additives, by controlling the particle size as well as the weight percent loading. Various layers of the coating may be applied, each containing different agents wherein the different agents may have different elution kinetics. The different layers may vary in thickness. It is apparent that layers such as capping layers can be used to control directionality of drug elution. Additives may be used that are thermally activated, or that enhance in vivo imaging during, for example, fluoroscopic or magnetic resonance imaging. These latter additives are referred to herein as imaging opaque substances. Radioactive additives may be used to locally deliver radiation therapy.

While various bioactive therapeutic agents such as antithrombotic drugs including heparin, paclitaxel, dexamethasone and rapamycin are most commonly proposed to aid the performance of stents, many others can also be used beneficially, either alone or in various combinations.

Therapeutic agents for a wide variety of applications can be used as additives with the coating for use with various devices. These agents include, but are not limited to, antithrombotic agents, anticoagulants, antiplatelet agents, thrombolytics, antiproliferatives, antiinflammatories, hyperplasia and restenosis inhibitors, smooth muscle cell inhibitors, antibiotics, antimicrobials, analgesics, anesthetics, growth factors, growth factor inhibitors, cell adhesion inhibitors, cell adhesion promoters and drugs that may enhance neointimal formation such as the growth of endothelial cells. Again, these therapeutic agents may be used alone or in various combinations, and may be in coatings that cover all surfaces of a device or only portions of a device.

Additives that are not bioactive and not elutable can be used, for example, various pigments, MRI-opaque additives or radiopaque additives (e.g., tantalum or gold) that are used to enhance imaging of an implanted device. Encapsulated void spaces may be used for enhanced echogenicity during procedures such as ultrasound. Pigments may be beneficially added to enhance direct visualization, for example, to provide a contrast against the blood of a surgical field. Pigments may also be used for printed indicia for various labeling or instructional purposes. Specialty pigments (e.g., luminescent) may be used for particular applications, such as enhancing visibility of devices (e.g., guidewires) in darkened catheter labs.

Mechanically induced release of an additive is possible. For example, pockets or layers of an additive may be captured within the coating. These pockets or layers may then be exposed to body fluids by penetrating the coating with a sharp surgical device or tool.

The term elution as described herein pertains to diffusion of an additive that occurs within a solvent, where the solvent may be any suitable fluid including body fluids. When the additive is contained within a copolymer, such as for controlled release within the body, the copolymer must wet in order for elution to take place.

The term diffusion is defined to mean the transport of matter by random molecular motion from one region in space to another. It is one of the processes that govern the elution of additives from a copolymer-additive formulation.

The coating material of the present invention can be exposed to high temperatures without degradation. For example, the coating material can be exposed to 330° C. for one hour with a resultant weight loss of less than five percent, preferably less than one percent, and more preferably less than 0.5 percent. Because of the high temperature capability and the inert character of the coating material, it lends itself to high temperature sterilization. Because it is not hydrolyzable, it is not adversely affected by conventional steam sterilization. Further, sterilization does not adversely affect elution profiles as long as the sterilization process does not affect any additive contained in the coating.

The coating is mechanically durable and tough. It is unaffected by exposure to body fluids because of its highly inert character. Coatings containing elutable additives retain good durability following elution of additives including particulate additives. The coating has good abrasion resistance for applications that may expose it to some degree of frictional wear. Further, the coating shows good resistance to tear propagation, even with high loading of additives.

BRIEF DESCRIPTION OF THE DRAWINGS

FIGS. 10A and 10B are scanning electron photomicrograph (about 100× and 200×, respectively) of two adjacent, curved expandable stent elements from balloon expandable stents, both provided with a coating of the present invention, steam sterilized and subsequently fully expanded.

DETAILED DESCRIPTION OF THE INVENTION

The present invention comprises a medical device in combination with a thermoplastic fluoropolymer, which is preferably an amorphous fluoropolymer. The fluoropolymer may optionally contain various additives. The thermoplastic fluoropolymer is a copolymer of tetrafluoroethylene (TFE) and perfluoroalkylvinylether (PAVE) that is free of cross-linking monomers and curing agents. The perfluoroakylvinylether may be perfluoromethylvinylether (PMVE), perfluoroethylvinylether (PEVE) or perfluoropropylvinylether (PPVE). The desirable mechanical characteristics, particularly tensile strength and toughness, are surprising given the absence of cross-linking monomers, curing agents, and process aids and fillers that would otherwise render such materials inadequately biocompatible.

The copolymer of TFE and PMVE is generally preferred, and may be made by emulsion polymerization techniques. The PMVE content ranges from 40 to 80% by weight, while the complemental TFE content ranges from 60 to 20% by weight. These materials have a secant modulus at 100% elongation of between 1 and 7 MPa (per ASTM D412-98, using ½ scale type IV dogbone with 250 mm/minute crosshead speed and 40 mm grip separation). The material has a durometer in the range of 50-90 Shore A.

Durometer measurements are made at room temperature (about 23° C.) by the method of ASTM D2240-91 using a Shore Durometer Type O with a Shore model CV-71200 Conveloader (Shore Instrument Co., Freeport, N.Y.). The durometer uses a hemispherical indenter of 1.2 mm radius. Samples tested by this method should be at least 6 mm thick; two or more samples may be stacked if necessary to achieve the minimum 6 mm thickness. Five durometer readings should be taken at five different points on each sample; these five readings are then averaged with the resulting mean value taken as the representative hardness value of the sample. Thickness measurements are the average of three or more measurements with a set of measuring calipers.

The PAVE component of the present invention is of the form $$F_2C=FCOC_nF_{2n+1}$$

where n, the number of carbon atoms in the side chain, equals 1 to 3. For n=1, the PAVE is PMVE; for n=2 the PAVE is PEVE and for n=3 the PAVE is PPVE.

Copolymers of TFE/PAVE can be analyzed for copolymer composition with various characterization techniques known to those of skill in the art, including both nuclear magnetic resonance (NMR) spectroscopy and Fourier transform infrared (FTIR) spectroscopy, with NMR as the primary method, complemented and confirmed by FTIR.

Various TFE/PAVE copolymer samples were analyzed by DSC using instruments such as a Perkin Elmer DSC7 equipped with Pyris for Windows® software version 3.72. When scanned as described previously, it was determined that the materials were amorphous.

Figure 1A:
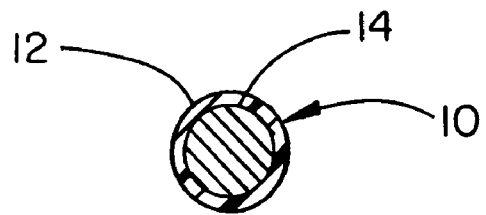
FIG. 1A is a transverse cross section of an elongate article of round cross section such as a metal wire (for example, as from a self-expanding stent or an electrical conductor), or a polymeric suture, provided with a coating of the present invention.

FIG. 1A is a transverse cross section of an elongate article 14 of round cross section such as a metal wire (for example, as from a self-expanding stent or an electrical conductor), or a polymeric suture, provided with a coating 12 of the present invention. Coating 12 covers the entire surface of the article 14 to create a coated article 10 which may be of any shape. Article 14 may be of any material other than the TFE/PAVE material of the coating. Typical metallic materials for article 14 may be metals such as stainless steels, nitinol alloys, platinum, gold, silver, etc. Alternatively, polymeric materials useful as article 14 include PTFE or ePTFE, polyethylene terephthalate (PET), polydimethylsiloxane (silicone), polyurethane (PU), or various other polymers known for use as medical devices. While the figure indicates that the entire outer surface of article 14 is provided with coating 12, it is apparent that only selected portions of the surface of article 14 may be covered as desired.

As coating 12 covers the entire surface (i.e., all surfaces) of article 14, it is referred to as a continuous coating, that is, an uninterrupted coating that fully covers the article 14. Partial coatings that are interrupted in any of a variety of possible ways (e.g., covering some surfaces while other surfaces remain uncovered, or dot-matrix pattern coatings, etc.) are considered to be discontinuous coatings.

Coatings may be in single or multiple layers. Any layer can contain one or more additives such as therapeutic agents. Any of the layers may be provided in porous (e.g., containing void spaces) forms or non-porous forms.

Figure 1B:
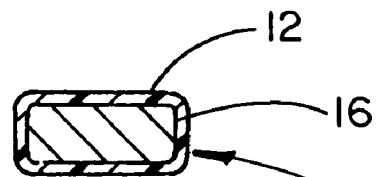
FIG. 1B is a transverse cross section of an article of rectangular cross section such as a stent element from a laser-cut balloon expandable stent, provided with a coating of the present invention.

FIG. 1B is a transverse cross section of an article 16 of rectangular cross section such as a stent element from a laser-cut balloon expandable stent, provided with a coating 12 of the present invention. Again, the article 16 may be made from a variety of materials and the coating 12 may be full or partial.

Figure 1C:
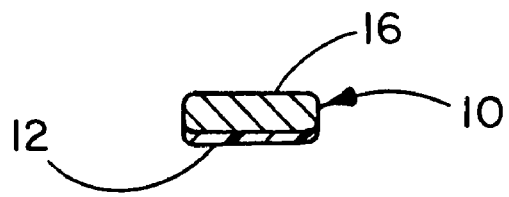
FIG. 1C is a transverse cross section of the same article shown by FIG. 1B except that a partial coating of the present invention is provided, on only one surface of the article.

FIG. 1C is a transverse cross section of the same article 16 shown by FIG. 1B except that a partial coating 12 of the present invention is provided, on only one surface of the article.

Figure 1D:
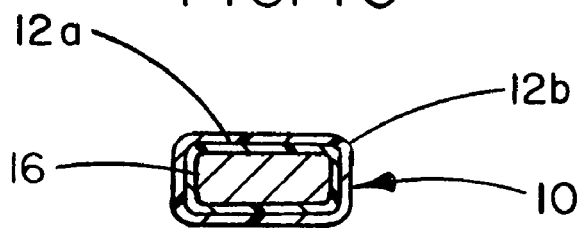
FIG. 1D is a transverse cross section of the same article shown by FIG. 1B except that first coating layer of the present invention is used that is provided with an additive, and then a second layer of the coating material is provided which does not contain an additive.

FIG. 1D is a transverse cross section of the same article 16 shown by FIG. 1B except that first coating layer 12a of the present invention is used that is provided with an additive, and then a second layer 12b of the coating material is provided as a capping layer which does not contain an additive.

Figure 1E:
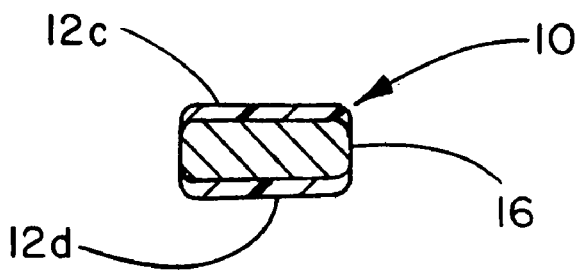
FIG. 1E is a transverse cross section of the same article shown by FIG. 1B except that two opposing sides of the article are provided with differently-filled coating layers.

FIG. 1E is a transverse cross section of the same article 16 shown by FIG. 1B except that two opposing sides of the article are provided with differently-filled coating layers 12c and 12d.

Figure 1F:
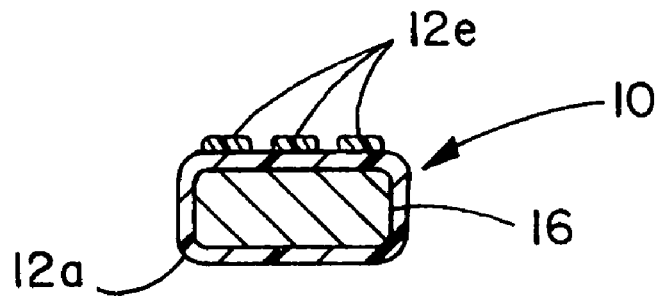
FIG. 1F is a transverse cross section of the same article shown by FIG. 1B except that one surface of the article is provided with a first continuous layer of the inventive coating containing a first additive, and a second discontinuous layer of the coating material is provided containing a second additive different from the first additive.

FIG. 1F is a transverse cross section of the same article 16 shown by FIG. 1B except that one surface of the article is provided with a first continuous layer of the inventive coating 12a containing a first additive, and a second discontinuous layer 12e of the coating material is provided containing a second additive different from the first additive. It is apparent that discontinuous layer 12e may be applied in any desired pattern, to any or all surfaces, etc. so that any desired pattern that is less than fully covering (i.e., continuous) may be produced.

Figure 1G:
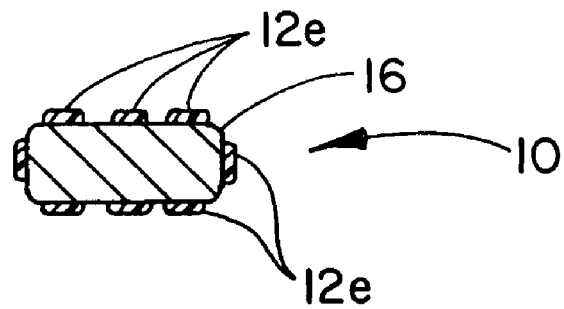
FIG. 1G is a transverse cross section of the same article shown by FIG. 1B except that discontinuous layers of the coating material are provided on both surfaces of the article, leaving portions of the article surface exposed between the discontinuous segments of the coating.

FIG. 1G is a transverse cross section of the same article 16 shown by FIG. 1B except that a discontinuous layer 12e of the coating material is provided on both surfaces of the article 16, leaving portions of the article surface exposed between the discontinuous segments of the coating.

Figure 1H:
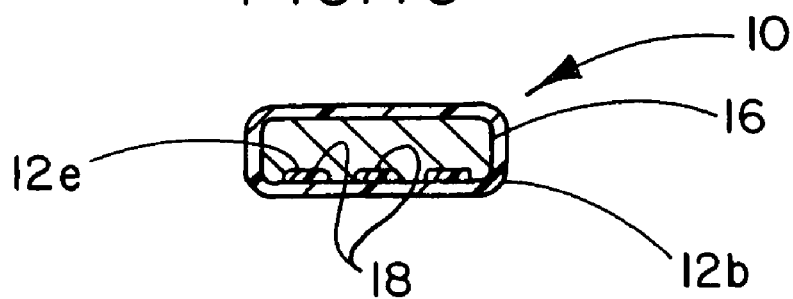
FIG. 1H is a transverse cross section of the same article shown by FIG. 1B except that the article is provided with pockets that are filled with a first coating of the inventive material with a continuous second layer of the material being used as a cap over the first layer contained by the pockets in the article.

FIG. 1H is a transverse cross section of the same article 16 shown by FIG. 1B except that the article is provided with pockets 18 that are filled with a first coating 12e containing an additive with a continuous second layer 12b of the material being used as a cap over the first layer contained by the pockets in the article.

Figure 1J:
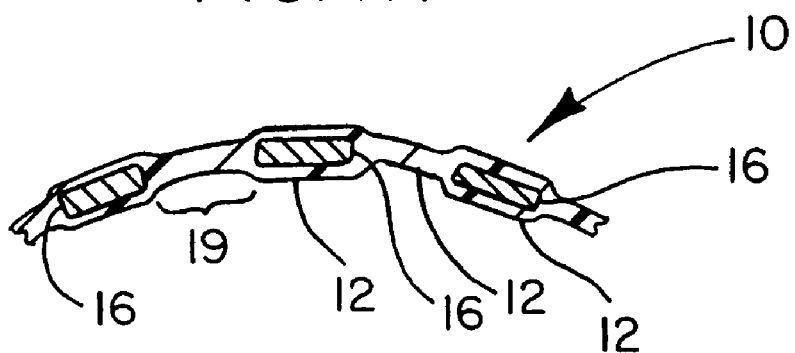
FIG. 1J is a cross section of multiple metallic stent elements provided with a continuous coating of the present invention that fully covers the stent elements and spans the interstices between the stent elements.

FIG. 1J is a cross section of multiple metallic stent elements of the present invention provided with a continuous coating that fully covers the stent elements and spans the interstices between the stent elements.

Figure 2A:
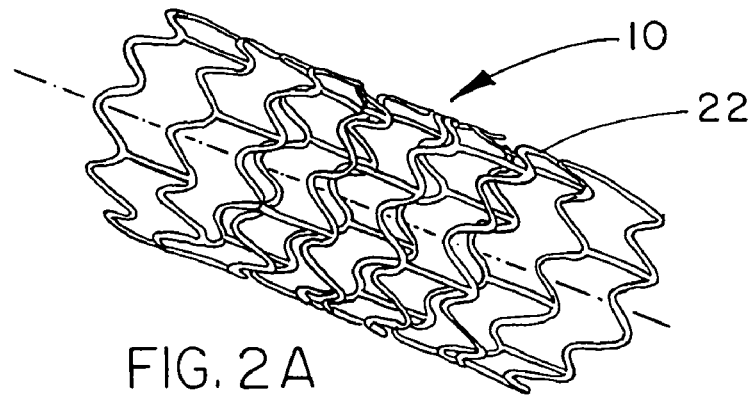
FIG. 2A is a perspective view of a laser-cut balloon expandable stent.

FIG. 2A is a perspective view of a laser-cut balloon expandable stent, intended as representative of stents generally. Stent 22 is provided with a coating of the thermoplastic fluoropolymer. As stated previously, the coating may be continuous or discontinuous, and may be provided with a variety of additives. The stent 22 is made from a suitable material such as any of various polymers or various metals including stainless steels or nitinols. While the stent shown is a balloon expandable stent, it is apparent that other types of stents including self-expanding stents may be coated as well. Stent 22 is provided with a series of apices 24 that are plastically deformable during diametrical expansion of the stent.

Figure 2B:
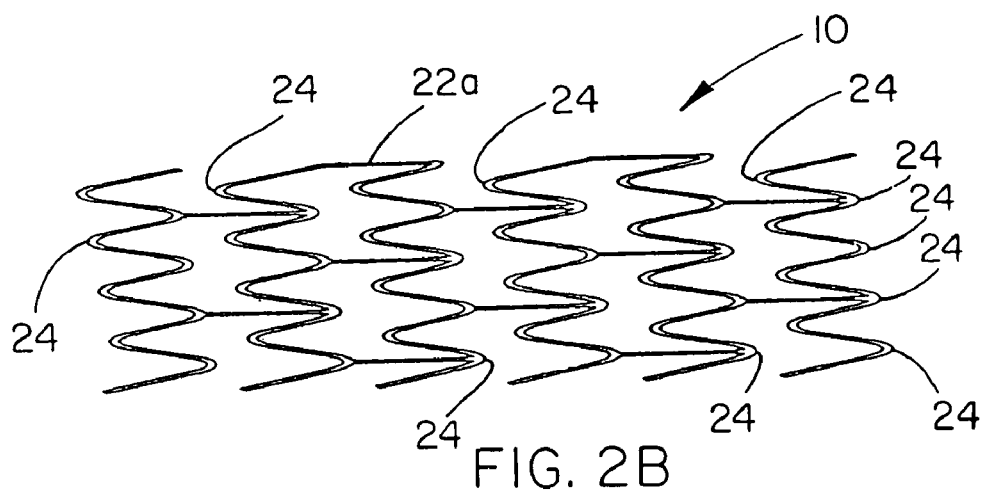
FIG. 2B is a top view of a section of the stent of FIG. 2A prior to deployment.
Figure 2C:
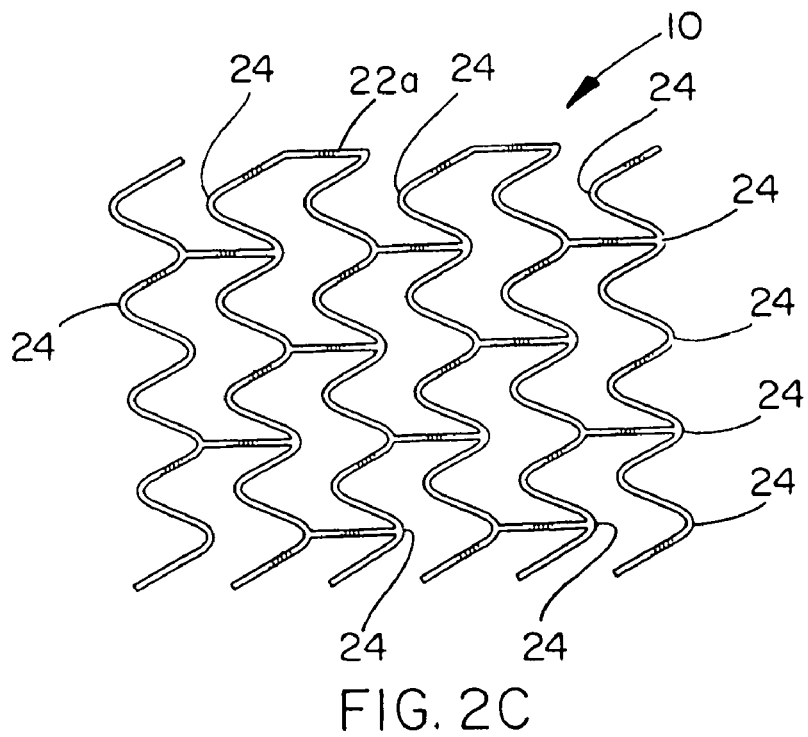
FIG. 2C is a top view of a section of the stent of FIG. 2A following deployment involving expansion of stent elements.

FIG. 2B is an enlarged top view of a flattened section 22a of the stent 22 of FIG. 2A prior to deployment. Apices 24 have a relatively small radius prior to expansion. FIG. 2C is an enlarged top view of the flattened section 22a of FIG. 2B following deployment involving expansion of stent elements. The previous relatively small radius of apices 24 is now increased due to plastic deformation resulting from stress applied during expansion. This deformation of stent apices 24 is problematic for many prior stent coatings in that they often crack or otherwise disrupt, with the result that the intended elution rate of any therapeutic agent contained in the coating can be significantly compromised. Macroscopic cracking of the coating may be ascertained by expanding an endoluminal device under ambient conditions in an amount of 50 percent (measured as change in the outside diameter of the device) in accordance with the instructions for use for the particular device (if applicable), followed immediately by visual examination (aided if necessary by 10× magnification). The coating is typically unaffected by such a normal stent expansion, even when the coating is provided with a high additive content. A device that is substantially free of such macroscopic cracks will have at most only a few minor cracks.

The capability of the coating of the present invention to be unaffected by deformation of stent components resulting from typical expansion (generally in the form of bending) can be demonstrated by providing a coating onto the surface of a wire. The coating should be applied in a desired amount, loaded with the desired additive in the desired amount. A straight length of wire having a round cross section of about 0.5 mm diameter should be used, with the wire being made of the same metal as a desired stent. After the coating has adequately dried, the wire is subjected to any sterilization procedure intended for the similarly coated stent. Following sterilization, the wire is bent at least 90 degrees at about the middle of its length, to a bend radius of 1.5 mm (i.e., to a bend radius of three times the wire diameter). The radius is measured to the inner meridian of the bent wire so that the wire can be bent around a form having a radius of 1.5 mm. With the present invention, typically no cracking or other similar disruption of the coating will occur.

Figure 3A:
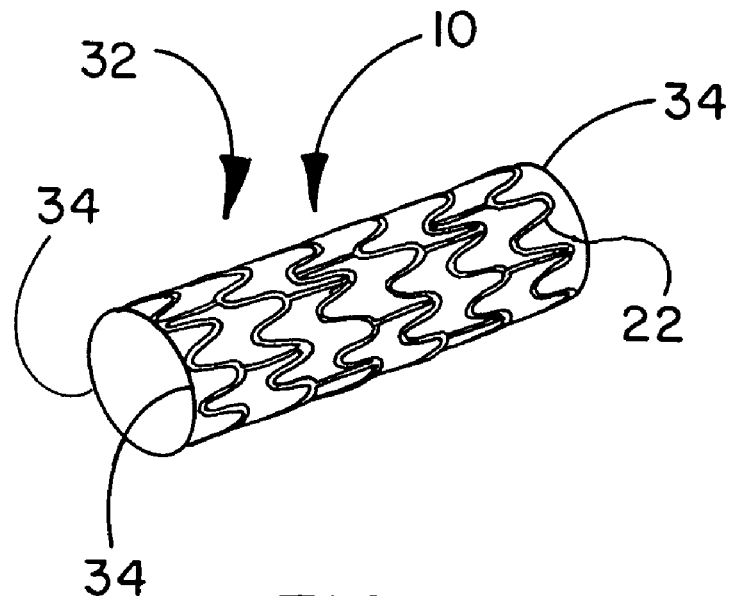
FIGS. 3A and 3B are perspective views of stent-grafts having a coating of the present invention.

FIG. 3A describes a stent-graft 32 of the present invention wherein stent 22 is provided with a graft covering 34. The graft covering may be provided over the inner surface of the stent as described by FIG. 3A, or over the outer surface of the stent, or both the outer and inner surfaces of the stent. Stent 22 may be any type of stent, including balloon expandable or self-expanding. The stent 22 described by FIG. 3A is intended only to be representative of stent forms generally and as such is not intended as limiting. The graft material may be made from a variety of materials including any known graft materials, for example, polyethylene terephthalate, silicone, polyurethane or ePTFE. Stent-graft 32 is beneficially provided with a coating of the present invention that may optionally contain any of a variety of additives as described previously.

A stent-graft such as described by FIG. 3A may be provided with a continuous coating of the coating material, wherein the TFE/PAVE coating covers the stent elements and the graft covering material. The entire graft covering may be coated including inner and outer surfaces. If the graft covering extends over only the inner or the outer surface of the stent (or any portion of those surfaces), the remaining surfaces of the stent that are not covered by the graft material may also be provided, or alternatively not provided, with the coating. Likewise, if desired, only the exposed portions of the stent 22 may be provided with the coating, leaving the graft material uncoated.

Because the coating adheres tenaciously to many types of surfaces, the coating may, for many inventive combinations of stent and graft materials, optionally be used as an adhesive to attach stent surfaces to the portions of the graft surfaces.

Figure 3B:
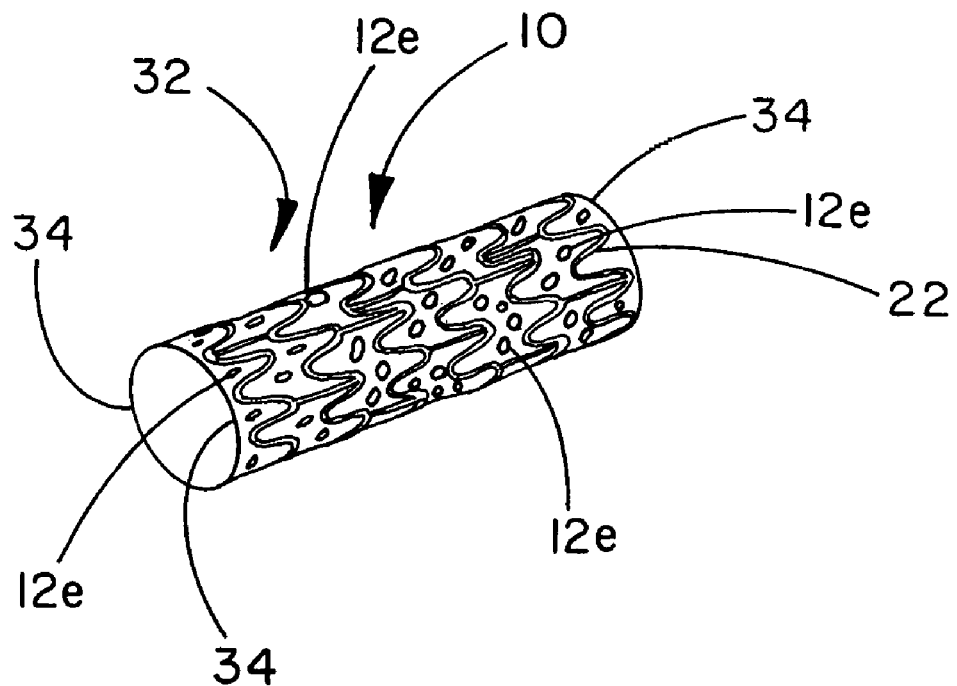

Alternatively, as shown by FIG. 3B, the stent-graft may be provided with a discontinuous coating 12e according to the present invention. This discontinuous coating can take a variety of forms as suggested by FIG. 3B. As shown, a dot-matrix coating 12e is applied over portions of the outer surface of the graft material covering the stent. As noted previously, the dot-matrix coating may be provided with any of various additives in desired amounts. Different dots within the dot-matrix pattern may be provided with different therapeutic agents if desired.

It is also apparent that different coatings may be used on different surfaces of a stent-graft. For example, a coating containing a first therapeutic agent may be provided to the luminal surface while another coating containing a second therapeutic agent different from the first may be applied to the exterior surface.

Figure 4A:
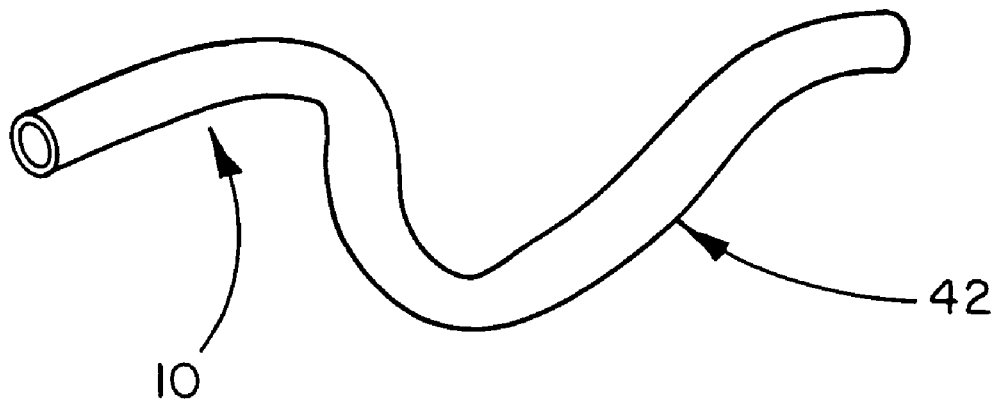
FIG. 4A is a perspective view of a vascular graft provided with a coating of the present invention.
Figure 4B:
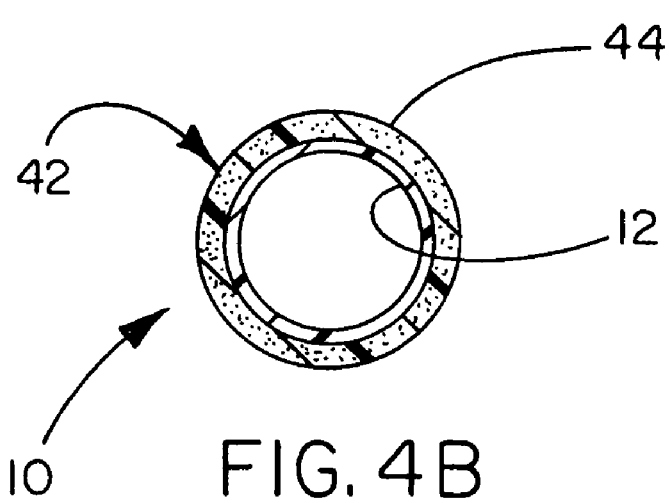
FIGS. 4B and 4C are transverse cross sections of coated vascular grafts of the present invention.
Figure 4C:
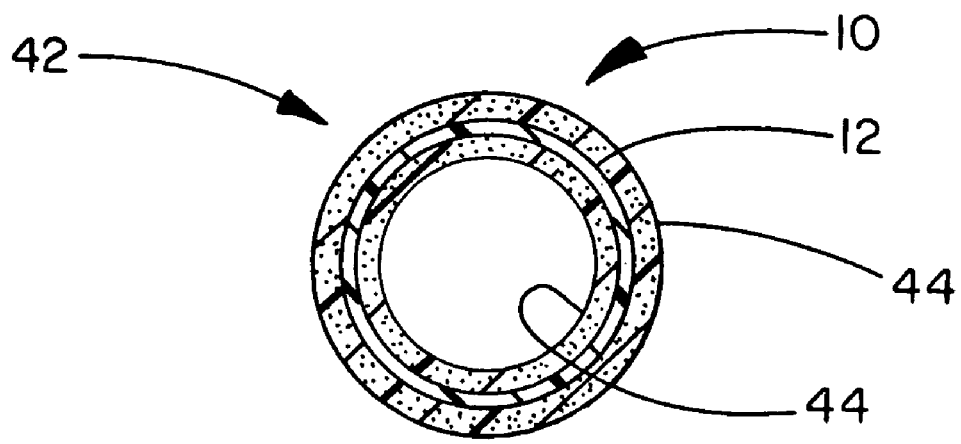

FIG. 4A describes a tubular vascular graft 42 provided with a coating of the present invention. The coating may be continuous or discontinuous (including, for example, dot-matrix patterns) as described previously. Additives may be added to the coating as desired for any of a variety of purposes, also as described previously. The vascular graft substrate material may be, for example, any known graft material such as ePTFE, PET or PU. As shown by the transverse cross section of FIG. 4B, the coating 12 may be provided on the luminal surface of the graft substrate 44. Alternatively, as shown by the transverse cross section of FIG. 4C, the coating 12 may be provided as a middle layer between inner and outer layers of vascular graft substrate 44. In another alternative, the coating may be provided on the abluminal surface of the graft.

If a porous vascular graft substrate is used, the coating may be impregnated into a portion or the entirety of the void space within the porous substrate.

Figure 4D:
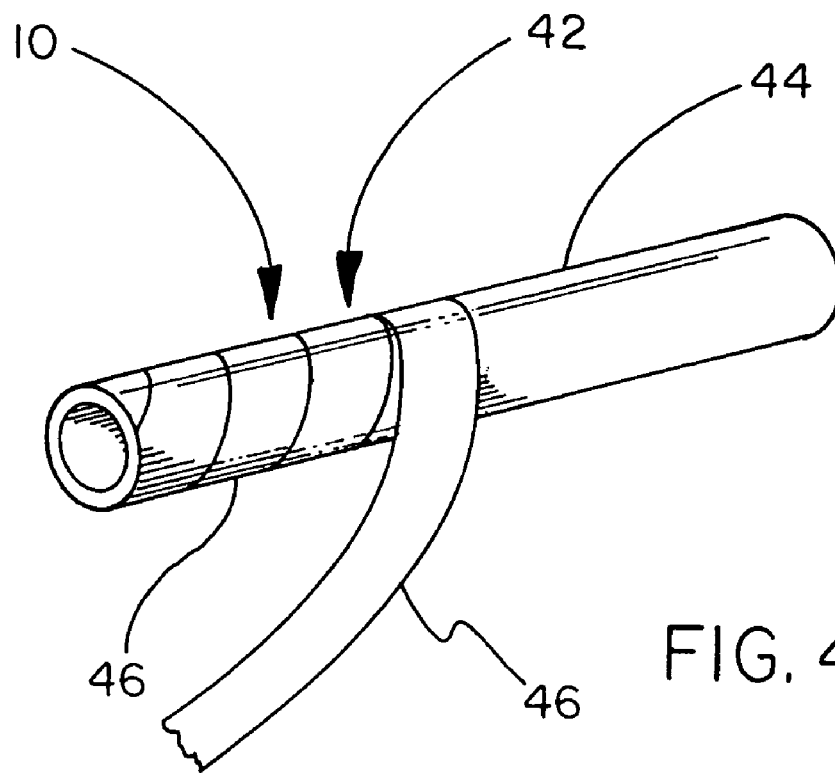
FIG. 4D is a perspective view of a helically-wrapped vascular graft of the present invention.

In another embodiment, the perspective view of FIG. 4D shows an ePTFE vascular graft substrate 44 provided with a helical wrap 46 of ePTFE film that has been provided as a narrow tape. ePTFE films are made generally as taught by U.S. Pat. Nos. 3,953,566 and 4,187,390 to Gore. The void space of the ePTFE film 46 may be impregnated with the coating described, or alternatively, the graft or the helically wrapped film may be coated as desired on any surface with the coating. In another alternative, because the coating may be provided in the form of a film, the helical wrap 46 may be in the form of the coating material.

In still another embodiment, the entire tubular vascular graft may be made from the coating material. Such a vascular graft may be provided with a variety of additives as noted previously. Such a graft may be formed with external mechanical support, such as molded in ridges, rings or struts. It is thus apparent that the coating may be applied in thicknesses as desired, to enhance the mechanical integrity or to provide other improved mechanical behavior to various medical devices in various ways. Coatings such as these may also incorporate additives.

Figure 5:
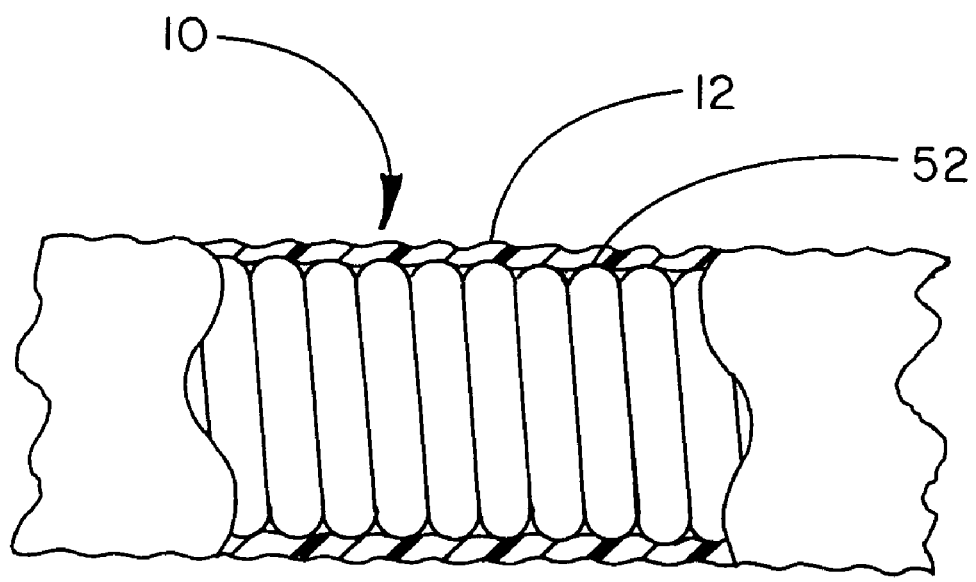
FIG. 5 is a longitudinal cross section of a catheter guidewire device or alternatively a helically wound electrical conductor provided with a coating of the present invention.

FIG. 5 is a longitudinal, partial cross-section of a catheter guidewire device 52 or alternatively a helically wound electrical conductor 52 provided with a coating 12. Coating 12 may be provided continuously as shown or alternatively in a discontinuous form if desired; likewise the coating may be provided with one or more additives if desired. The coating 12 may also be provided as a helical wrap of a tape made from the coating material.

Figure 6A:
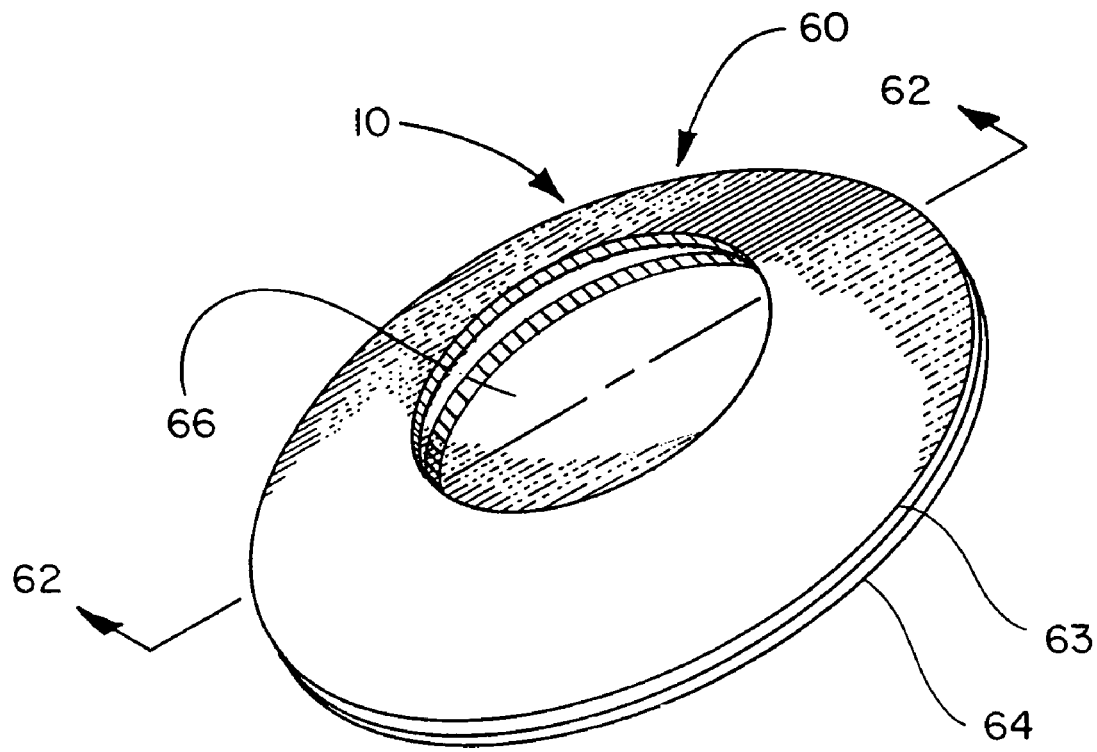
FIGS. 6A and 6B are isometric and cross sectional views of a keratoprosthesis using the coating material of the present invention.
Figure 6B:
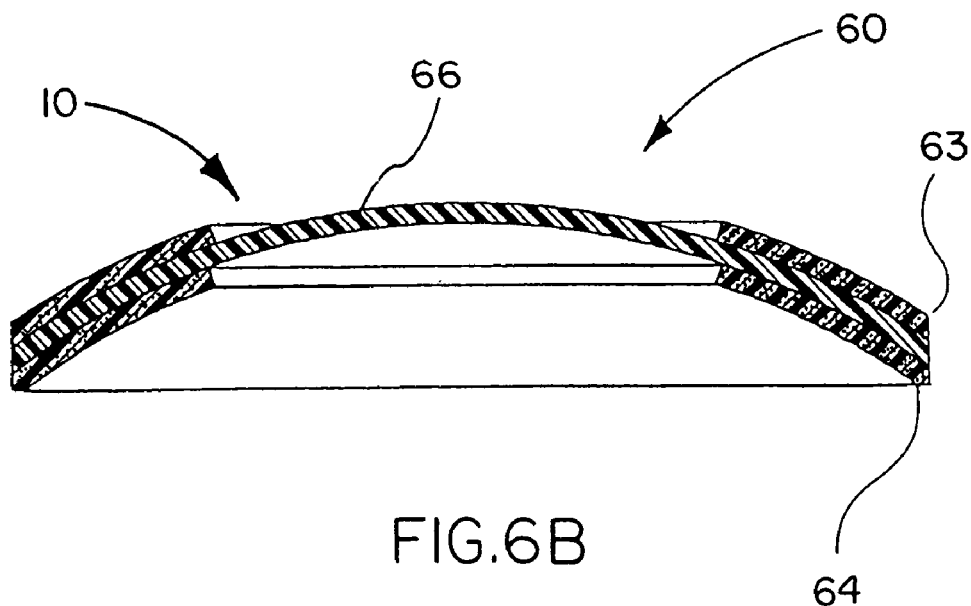

FIG. 6A is an isometric view of an implantable cornea prosthesis or keratoprosthesis. Keratoprosthesis 60, preferably having an ePTFE peripheral skirts or skirts 63 and 64, is attached to a fluoropolymer cornea substitute 66. The skirts have a porosity that can be tailored to promote rapid ingrowth and attachment into surrounding native tissue. FIG. 6B is a cross-sectional view of an implantable keratoprosthesis 60, taken along section lines 62, showing a first ePTFE skirt layer 63, a second ePTFE skirt layer 64 and an polymeric cornea substitute layer 66. The cornea substitute layer 66 can be shaped to conform to surrounding native tissue and have a thickness, flexibility and creep resistance suitable for long term ocular implantation. In addition, the ePTFE skirts can be pre-treated with a wetting agent such as poly(vinyl alcohol) to promote rapid post implant wetting, which enhances to initial anchoring to surrounding tissue. Keratoprosthesis 60 can be produced, for example, by a lamination process in which one or more layers of ePTFE 63, 64 are aligned onto a polymeric corneal layer 66 and compression molded to form a laminate.

The material of polymeric corneal layer 66 can also be used to form an implantable lens or other light-transmitting device. Additives such as ultraviolet absorbers, pigments or therapeutic agents can also be incorporated into the polymeric layer 66, or into other optical devices such as lenses or transparent coatings.

The following examples are intended to describe various embodiments possible with the scope of the present invention. As such, they are not intended to be limiting with regard to variables such as stent type, choice of PAVE polymer, coating thickness, surface on which a coating is placed, coated vs. uncoated portions of devices, therapeutic agent contained in one or more layers of the coating, type of therapeutic agent incorporated, etc.

EXAMPLE 1

TFE/PMVE Film Evaluation of Thermal Stability of the Material

A sample of TFE/PMVE copolymer was made by emulsion polymerization resulting in average emulsion particle size of 32 nanometers (particle size estimated using light scattering methods), exhibiting the following properties: mean tensile strength of 15.2 MPa, mean 100% secant modulus of 2.37 MPa, average tensile set of 0%, and PMVE content of about 66% by weight. This copolymer sample was compression molded to produce a thin film of 0.18 mm thickness. Approximately 15 micrograms of the thin film in the form of a square sample of about 0.2 mm length per side was utilized for determination of the copolymer degradation temperature by themogravimetric analysis. The high-resolution scan covered the temperature range of 0-800° C. at heating rate of 20° C. per minute. Test results indicated that material degradation initiated at approximately 400° C., with a weight loss of less than about 0.5% at 400° C.

In an isothermal sweep, in which temperature was held at 330° C. for 1 hr, the same copolymer experienced a total weight loss of less than about 0.5%. The exceedingly low weight loss associated with these severe thermal conditions demonstrates the high thermal stability of this thermoplastic material.

A similar procedure can be used to demonstrate the thermal stability of a drug-containing TFE/PMVE material. The drug is first eluted from the material, and then the thermogravimetric analysis is performed as described above.

EXAMPLE 2

TFE/PMVE Film Having Pockets Loaded with Chlorhexidine Dihydrochloride

Thin films of TFE/PMVE copolymer described by Example 1, were produced via melt extrusion at temperatures exceeding 200° C. A film possessing a thickness of approximately 0.2 mm was used to construct a laminate with pockets of chlorhexidine dihydrochloride, an antimicrobial agent. A polypropylene template with 0.7 mm diameter holes arranged in a rectangle pattern was made to facilitate manufacturing of the device. The holes were evenly spaced approximately 2 mm apart, from edge to edge. This template was placed on top of one of the TFE/PMVE extruded sheets, then dusted with chlorhexidine dihydrochloride. The template was removed, leaving a dot-matrix pattern of the drug on the surface of the extruded film. A second sheet of extruded polymer was gently placed on top of the first sheet. The composite of polymer sheets and drug was wrapped in aluminum foil, placed between two metal plates, heated in an oven set at 115° C. for 15 minutes, removed from the oven, immediately pressed between the two hot metal plates for 15 minutes, and then removed from the metal plates and aluminum foil. This process created encapsulated drug pockets between the polymer films.

The composite exhibited excellent bond characteristics. The bond strength was so high that all attempts to delaminate the polymer films resulted in destruction of the composite.

Figure 7A:
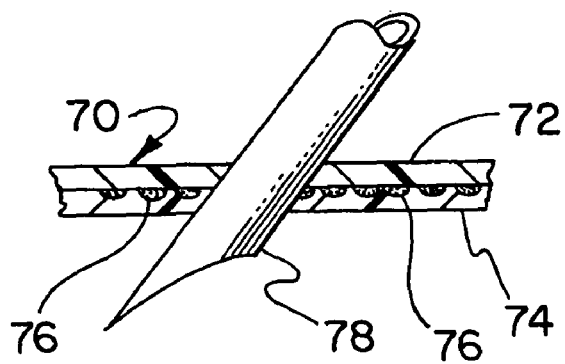
FIG. 7A is a cross-sectional view of a composite two-layered device containing a dot-matrix pattern of a therapeutic agent applied between the two layers, shown as punctured by a needle.
Figure 7B:
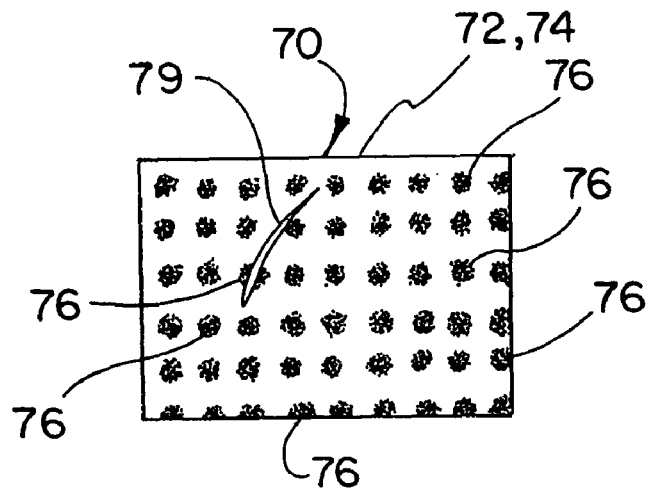
FIG. 7B is a top view of the two-layered device of FIG. 7A, shown following removal of the puncturing needle.

A cross-sectional view of the composite device 70 is shown in FIG. 7A. First film layer 72 is provided as a cap over second film layer 74, with film layer 74 being provided with a dot-matrix pattern 76 of a desired drug. The device 70 is shown as it would appear when punctured with a needle 78. FIG. 7B illustrates device function following removal of the puncturing needle, allowing immediate release of drug from dots 76 that are affected by the needle puncture 79.

Figure 7C:
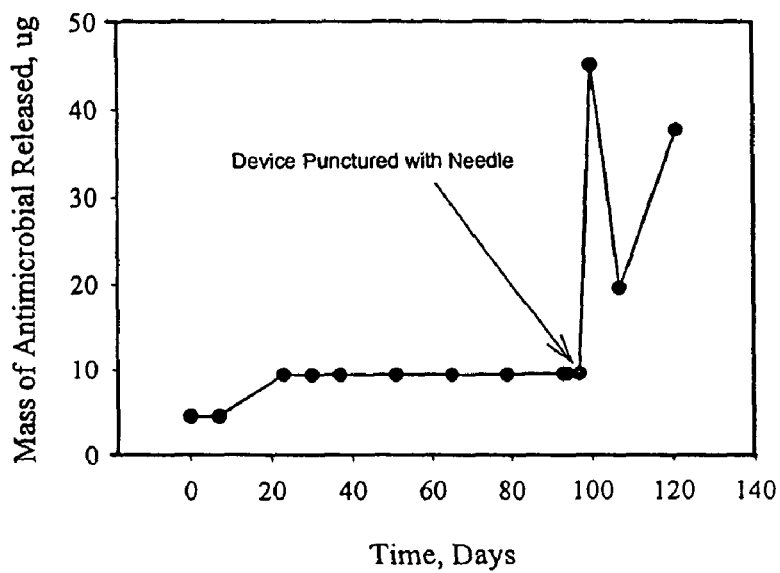
FIG. 7C is a graph describing the release of drug from the device of FIGS. 7A and 7B, indicating a substantial, abrupt increase in the release rate following puncture with a needle.

An approximately 1 cm by 1 cm square of finished material was placed into phosphate buffered saline (PBS) at 37° C., periodically sampled for antimicrobial content, and punctured with a 16-gauge needle. The release of the chlorhexidine dihydrochloride as a function of puncturing the composite and time in solution is shown in FIG. 7C. It is important to note that chlorhexidine dihydrochloride was continuously released at a minimal level until the composite was punctured with the needle. Thus, an additional dose of the drug can be delivered on demand as a consequence of puncturing drug pockets.

EXAMPLE 3

Vascular Graft Coated with TFE/PMVE Containing Dexamethasone

The copolymer of Example 1 was obtained in a 4 wt % solution of FC-75. The working drug formulation was a mixture of 2 ml of 4 wt % polymer, 8 ml of FC-75, and 150 mg of dexamethasone (52 wt % drug based on total weight of coating solids; dexamethasone obtained from Pharmacia & UpJohn, Kalamazoo Mich.). The formulation was made by weighing dexamethasone into a test tube, adding FC-75, vortexing vigorously to complete mixing, adding the polymer, and ensuring complete mixing with additional vortexing.

A 10 cm length of Gore-Tex Vascular Graft (part number UT05070L, WL Gore & Associates, Flagstaff Ariz.) was used to demonstrate the drug release coating. The 5 mm inside diameter graft was mounted onto a mandrel for coating. The mandrel was rotated by hand as an airbrush (Badger standard set model 350 airbrush set at 220 KPa gauge air pressure, Badger Air Brush Co., Franklin Park, Ill.), held at a constant distance of approximately 3.8 cm from the graft surface, was moved back and forth across the graft while spraying a coating of the above-described polymer-drug formulation. The vascular graft was continuously spray-coated for approximately 10 minutes, after which time the graft was transferred to an oven set at 60° C. for 2 minutes. Microscopic examination of cross sections of such a coated graft indicated that the coating penetrated into the void spaces of the microstructure of the porous ePTFE vascular graft. Physical examination of these coated graft samples indicated that the coating was well adherent.

After the drug layer was applied, the vascular graft was divided into two sections, 5 and 4 cm in length. A slight contraction of the graft in the longitudinal direction was noted after the coating was applied, as the total length measured about 9 cm after coating. This contraction was believed to be the result of drying of the relatively heavy coating. The 5 cm section was coated with a capping layer that did not contain any drug. The capping formulation consisted of 2 ml of 4 wt % polymer mixed with 8 ml of FC75. The solution was sprayed in a similar manner as above in five 30 second spray intervals. Spraying intervals were separated by a 15 second interval of not spraying. The 4 cm section was sprayed in eight 30 second intervals, alternating with 15 second intervals of not spraying. The 5 cm long section was taken for determination of total drug loading. Loading determinations were performed by placing the sample in 5 ml of ethanol in a glass test tube for 15 hours at 55° C. After ethanol extraction, the solution was analyzed for dexamethasone content using a UV spectrophotometer (dexamethasone wavelength: 244 nanometers). The loading was determined to be 7.5 +/−1.0 mg/cm graft length.

It is apparent that there are many different possible applications of the coating polymer, with or without a therapeutic agent, to vascular grafts made of virtually any known graft materials. For example, TFE/PMVE not containing any drugs (e.g., the capping material) could also have been spray coated directly onto the vascular graft surface. The coating may be applied between layers of the vascular graft, or may be applied to the luminal surface of a vascular graft.

EXAMPLE 4

Wires Coated with TFE/PMVE Containing Dexamethasone

A sample of the same TFE/PMVE copolymer of Example 1 was prepared. The polymer was dissolved in FC-75 to obtain a 4 wt % solution.

A spray formulation was consisting of a dexamethasone emulsion plus dispersion was investigated first. Two ml of this 4 wt % polymer solution was diluted with 8 ml of FC-75 and mixed in a 15 ml plastic test tube, with periodic vortexing. 12.5 mg of dexamethasone as a powder and 200 microliters of a saturated ethanol solution containing dexamethasone (approximately 15 mg/ml of dexamethasone) were added to the solution. The system was vortexed for 1 minute to ensure complete mixing. It contained 10 wt % drug based on total weight of coatings solids, with wt % drug content calculated as drug mass/(drug +polymer mass), multiplied by 100.

The system was then coated onto a straight length of 0.51 mm diameter silver-plated copper wire. This wire was intended to serve as a model of a structural element used in various medical devices, such as stents. The wire was spray-coated with the polymer using a Badger standard set model 350 airbrush, for 1 minute, at an air pressure of 220 KPa, and placed in an air forced furnace for 5 minutes at 60° C. Ethanol extraction of such a coated wire segment followed by UV spectrophotometric analysis yielded 6.4 micrograms of drug per cm of wire length. After the drug layer was applied, a capping layer that did not contain any drug was sprayed onto the wire. The capping formulation consisted of 2 ml of 4 wt % polymer mixed with 8 ml of FC-75. The solution was sprayed in a similar manner as described above. The total coating on the wire was approximately 10 microns thick.

A spray formulation consisting of a single emulsion of dexamethasone was also investigated. The working formulation was made by combining 2 ml of the 4 wt % polymer solution with 8 ml of FC-75 and allowing the system to mix in a 15 ml plastic test tube, with periodic vortexing. 400 microliters of a saturated ethanol solution containing dexamethasone (approximately 15 mg/ml of dexamethasone) was added to the copolymer solution. The system was vortexed for 1 minute before coating to ensure complete mixing. The coating on this wire was approximately 5 microns thick. The coating contained 4.1 wt % drug based on total weight of coating solids. Ethanol extraction of wire segment followed by UV spectrophotometric analysis yielded 17.5 micrograms per cm of wire length.

Figure 8A:
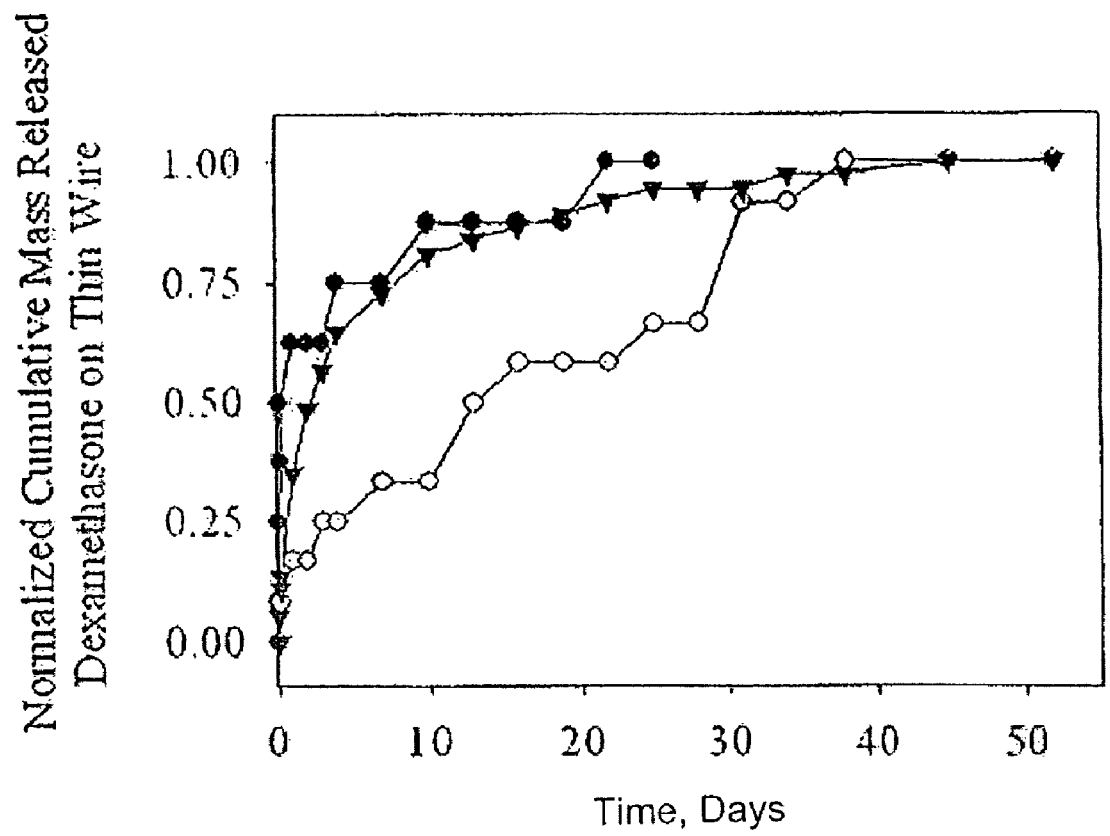
FIG. 8A is a graph of normalized cumulative mass of dexamethasone released from three samples of wires provided with different polymer-drug coating formulations demonstrating a range of possible release kinetics. The open circles depict the emulsion plus dispersion formulation, filled circles the single emulsion and filled triangles the powder coating formulation.
Figure 8B:
FIG. 8B is a scanning electron photomicrograph (SEM; about 20×) of a straight, 0.5 mm diameter wire provided with the coating of the present invention, and subsequently bent.

A powder coating formulation was also investigated. Two ml of the 4 wt % polymer solution was combined with 8 ml of FC-75, then mixed in a 15 ml plastic test tube, with periodic vortexing. A polymer base coat was applied to the wire for 2 min. While still wet, the wire was suspended in a blender that had been pulsed briefly to air suspend dexamethasone. A capping layer that did not contain any drug was sprayed on the wire. The capping formulation consisted of 2 ml of 4 wt % polymer mixed with 8 ml of FC-75. The solution was sprayed in a similar manner as described above. The coating on this wire was approximately 5 microns thick. No theoretical loading was calculated. Ethanol extraction of wire segment followed by UV spectrophotometric analysis yielded 63.5 micrograms per cm wire length. Samples of the coated wires were taken for SEM analysis and the determination of drug release. The graph of FIG. 8A demonstrates the extended elution times possible with the different emulsion spray formulations, based on three samples made as described above (open circles depict the emulsion plus dispersion formulation, filled circles depict the single emulsion and filled triangles depict the powder coating formulation). Each of the three types of coating resulted in smooth and uniform surfaces before and after drug release as evidenced by SEM analysis. These findings suggest that drug elution occurred on a molecular level. FIG. 8B is an SEM (about 20× magnification) showing the crack-free mechanical integrity of the single emulsion coating of the different emulsion spray formulation process when the coated wire was bent in excess of a 90 degree angle, at a radius of about 1.1 mm as measured to the inside meridian of the bent wire.

In all of these embodiments, the TFE/PMVE coating remained intact after complete elution of the drug.

EXAMPLE 5

Balloon-expandable Stent Coated with TFE/PMVE Made with Standard Emulsion, No Drug A sample of TFE/PMVE copolymer, made from emulsion polymerization resulting in an average emulsion particle size of about 120 nanometers, was prepared having the following properties: mean tensile strength of 26.7 MPa, mean 100% secant modulus of 2.7 MPa, mean tensile set of 12%, and PMVE content of about 60% by weight. Neither this TFE/PMVE copolymer nor any TFE/PMVE copolymer used in any the examples contained any cross-linking monomers or curing agents or system. The copolymer was added to FC-75 fluorinated solvent, to make a 4 wt % solution. The FC-75 fluorinated solvent, 3M Fluorinert, was obtained from 3M Specialty Chemicals Division, St. Paul, Minn. 55144. The working formulation was made by diluting 2 ml of the 4 wt % polymer solution with 8 ml of FC-75 and allowing the system to mix in a 15 ml plastic test tube, with periodic vortexing.

Stents made in accordance with the teachings of U.S. Pat. No. 5,925,061 to Ogi, et al. were laser cut and polished by Laserage Technology Corp., Waukegan, Ill. 60087. All stents were cut from 316H stainless steel tubing possessing a wall thickness of 0.127 mm. The outside diameter of the stents was 1.57 mm while the length was 21 mm.

Each stent was temporarily placed onto a small wire for handling during the coating process. The wire was curved at one end to prevent the stent from slipping off. Once secured on the wire, the stent was dipped into the polymer solution, sprayed with compressed air to minimize any bridging of the coating between adjacent stent elements, and placed in an air forced furnace for 5 minutes at 60° C. The dipping procedure may be repeated if multiple coatings are desired. For this example the dipping procedure was repeated 4 times. Scanning electron photomicrographs of uncoated and coated stents were taken before and after diametrically expanding up to 4.5 mm inner diameter with an angioplasty balloon. The expansion ratio was approximately 3. Scanning electron micrographs of the coated stent surfaces after balloon expansion show complete and uniform coverage of the metal surface by the polymer coating, regardless of stent shape or geometry. Subsequent to balloon expansion a portion of the stent surface was scraped with a surgical blade to test for coating integrity. This was done by positioning the blade perpendicular to the surface of the stent element, applying a downward force and dragging the blade a short distance.

Figure 9:
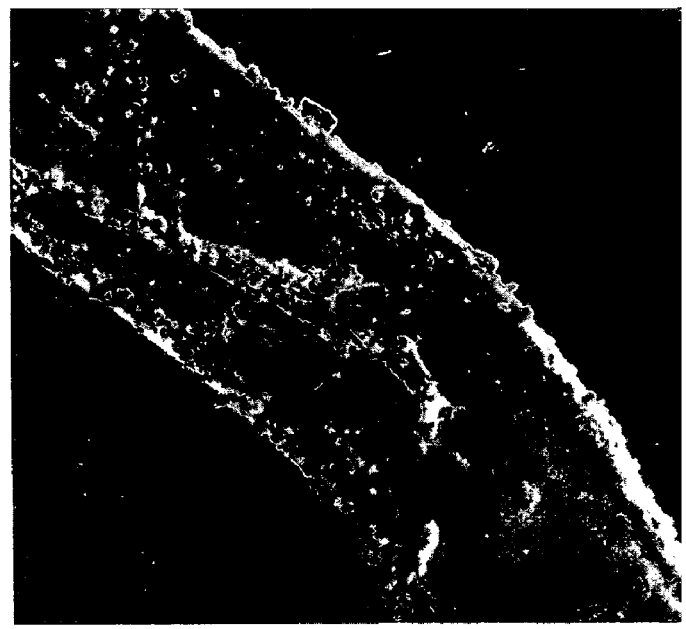
FIG. 9 is a scanning electron photomicrograph (about 260×) of a stent element provided with the coating of the present invention following a scrape test with a scalpel blade.

FIG. 9 is a scanning electron photomicrograph (about 260× magnification) of the surface after the scrape test. The coating was only removed from the regions of blade contact. There appeared to be no gross delamination or shrink-back of the coating from the scraped region, indicating good adhesion of the coating.

EXAMPLE 6

Balloon-expandable Stent Coated with TFE/PMVE, No Drug

Other stents were coated with a polymer solution, which included the copolymer of TFE/PMVE described by Example 1. The polymer was dissolved in FC-75 to obtain 4 wt % solution. The working formulation was made by diluting 2 ml of the 4 wt % polymer solution with 8 ml of FC-75 and allowing the system to mix in a 15 ml plastic test tube, with periodic vortexing.

Coated stents were made and tested as described above for Example 5, yielding the same results regarding complete and uniform metal surface coverage and smoothness of the coating surface. No gross delamination of the coating was observed.

Coated stents made in this manner were steam sterilized (134° C. at 216 KPa for 12 minutes followed by a 30 minute drying cycle), balloon expanded to 3 mm diameter, and subjected to SEM analysis for determination of coating stability. The scanning electron photomicrographs of FIG. 10A (about 100× magnification) and FIG. 10B (about 200× magnification) show that after processing and expansion, the polymer coating was still adherent to irregular shapes, without any evidence of delamination or tearing, demonstrating coating integrity even after steam sterilization and subsequent expansion.

EXAMPLE 7

Balloon-expandable Stent Coated with TFE/PMVE Containing Dexamethasone

A copolymer-drug coating, where the TFE/PMVE copolymer is described by Example 1, was applied to balloon expandable stents of the same type as used in Example 5. The amount of dexamethasone was approximately 400 micrograms per stent, applied by single emulsion spray coating as was done previously with the wire coating in Example 4. The stent was balloon expanded to a diameter of 3.5 mm prior to initiating drug release studies. SEM analysis of the device surface subsequent to balloon expansion evidenced no delamination or separation of the coating from the metal. Release studies performed on another of these coated balloon expanded stents demonstrated that the drug was released in a controlled fashion. After completion of release studies, the sample underwent SEM analysis. The coating showed no delamination or separation from the metal. The polymer-drug coating thickness was estimated to be approximately 3 microns.

EXAMPLE 8

Balloon-expandable Stent Coated with TFE/PMVE Containing 60 wt % Dexamethasone

A sample of the same TFE/PMVE copolymer, made as described for Example 1, was prepared. The polymer was dissolved in FC-75 to obtain a 4 wt % solution. One hundred and twenty mg of dexamethasone as a powder was weighed into a 15 ml plastic test tube, 6 ml of FC-75 was added, and the system was mixed vigorously to ensure complete mixing. Two grams of the 4 wt % TFE/PMVE polymer solution was added and the mixture was vortexed. This formulation is 60 wt % dexamethasone on a total solids basis. The formulation was applied to balloon expandable stents of the same type used in Example 5. These stents were coated with the copolymer-drug solution through a dip coating processes in which the stents were suspended from a thin wire, immersed in the formulation, sprayed with compressed air at 1.7 KPa air pressure, and placed in a convection oven set at 60° C. briefly for compete drying. One group of stents received 1 dip coating and another group 3 dip coatings. Stents from each group were distended with the use of 3.5 mm PTFE balloons before and after sterilization with EtO at a total cycle time of 15 hours, including an EtO sterilization time of 1.3 hours at 67.7° C. Stents were examined with the use of a light microscope at magnification of up to 90×. Microscopic examination of samples before and after expansion with or without EtO sterilization showed the coating to be tough, and well adhered, and without evidence of cracking.

Figure 11A:
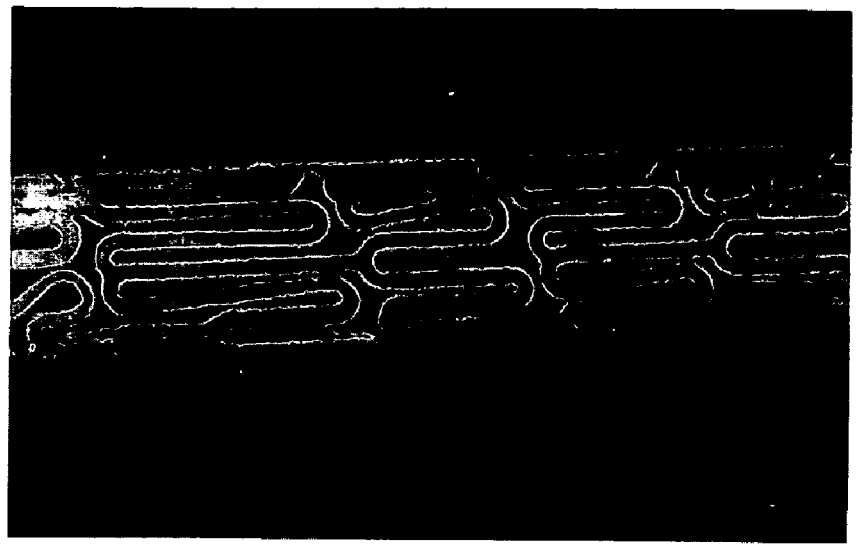
FIGS. 11A and 11B are light micrographs (about 15×) a stent coated with three layers of drug/polymer, and subjected to ethylene oxide (EtO) sterilization at 67.7° C., before and after expansion with a balloon.
Figure 11B:
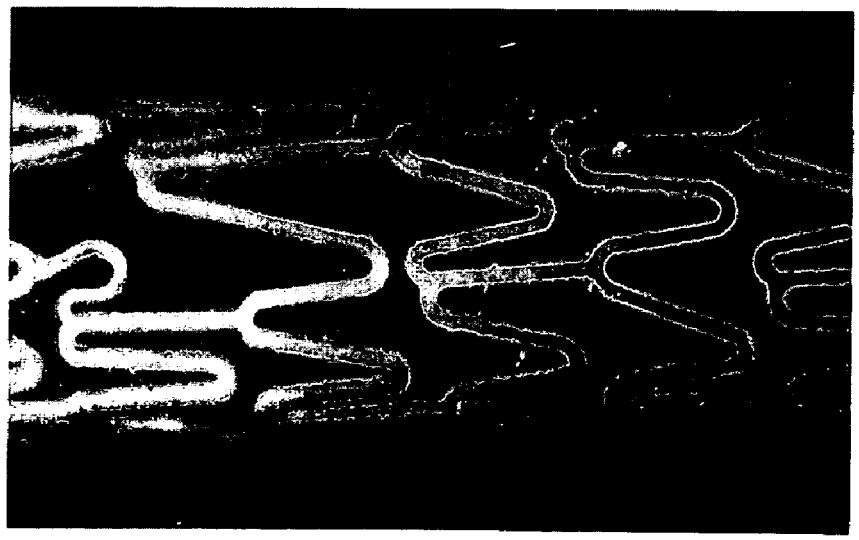

FIG. 11A is a light micrograph (about 15× magnification) of a drug/polymer coated stent according to this example that has been subjected to EtO sterilization at 67.7° C., before expansion. Three drug-polymer coat layers were applied to this stent as described above. FIG. 11B (about 15× magnification) describes the same stent after balloon expansion using a 3.5 mm diameter ePTFE/elastomer composite balloon (made generally as taught by example 7 of U.S. Pat. No. 6,120,477 to Campbell et al.). It is anticipated that virtually any suitable commercially available catheter balloon of suitable size would provide the same stent expansion results.

EXAMPLE 9

Balloon-expandable Stent Coated with TFE/PPVE, No Drug

A sample of TFE/PPVE copolymer was obtained, which was synthesized by emulsion polymerization, resulting in average emulsion particle size of 83 nanometers, exhibiting the following properties: mean tensile strength of about 12.2 MPa, mean 100% secant modulus of 4.30 MPa, average tensile set of 31%, and PPVE content of about 56% by weight. The polymer was dissolved in FC-75 to obtain a 20 wt % solution. The working formulation was made by diluting 2 ml of the 20 wt % polymer solution with 8 ml of FC-75 and allowing the system to mix in a 15 ml plastic test tube, with periodic vortexing.

Balloon expandable stents of the same type used in Example 5 were utilized. Each stent had a small wire temporarily looped through one end for handling during the subsequent dip-coating process. Once secured on the wire, the stent was dipped into the polymer solution, sprayed with compressed air, and placed in an air forced furnace for 5 minutes at 60° C. The dipping procedure was repeated to bring the total number of layers to 2. A portion of the TFE/PPVE coated stents were then expanded without being EtO sterilized using a balloon as described for Example 8, and examined with the use of a light microscope. Additional coated stents underwent EtO sterilization with a total cycle time of 15 hours, including an EtO sterilization time of 1.3 hours at 67.7° C. After sterilization the stents were expanded using a balloon of the type described for Example 8, and examined with a light microscope at magnification of up to 90×. Microscopic examination of samples before and after expansion with or without EtO sterilization showed the coating to be tough, well adherent, and without evidence of cracking.

Figure 12A:
FIGS. 12A and 12B are light micrographs (about 15× and 30×, respectively) of a TFE/PPVE polymer-coated stent that has been subjected to EtO sterilization at 67.7° C., before and after balloon expansion.
Figure 12B:

FIG. 12A is a light micrograph (about 15× magnification) of a TFE/PPVE polymer coated stent according to this example that has been subjected to EtO sterilization at 67.7° C. before balloon expansion. FIG. 12B is a light micrograph (about 30× magnification) of the same stent following balloon expansion using a balloon as described in Example 8.

EXAMPLE 10

Balloon-expandable Stent Coated with TFE/PPVE Containing 60 wt % Dexamethasone

Approximately 60 mg of dexamethasone powder was weighed into a 15 ml plastic test tube, 6 ml of FC-75 was added, and the system was mixed vigorously to ensure complete mixing. Two hundred mg of 20 wt % TFE/PPVE polymer solution (made per Example 9) was added and the mixture was vortexed. This formulation is 60 wt % dexamethasone on a total solids basis. Balloon expandable stents of the same type used in Example 5 were utilized. Each stent had a small wire temporarily looped through one end for handling during the subsequent dip-coating process. Once secured on the wire, the stent was dipped into the polymer solution, sprayed with compressed air at 1.7 KPa air pressure, and placed in an air forced furnace for 5 minutes at 60° C. Stents were distended with the use of 3.5 mm PTFE balloons before and after sterilization with EtO at a total cycle time of 15 hours, including an EtO sterilization time of 1.3 hours at 67.7° C.

Stents were examined with the use of a light microscope at magnification of up to 90×. Microscopic examination of samples before and after expansion with or without EtO sterilization showed the coating to be tough, well adherent, and without evidence of cracking.

Figure 13A:
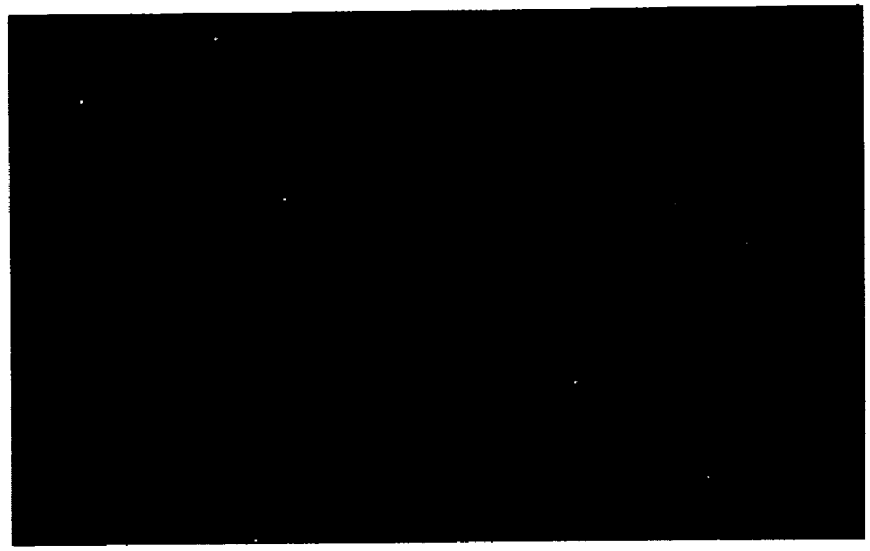
FIGS. 13A and 13B are light micrographs (about 15× and 30×, respectively) of a drug-TFE/PPVE polymer-coated stent that has been subjected to EtO sterilization at 67.7° C., before and after balloon expansion.
Figure 13B:
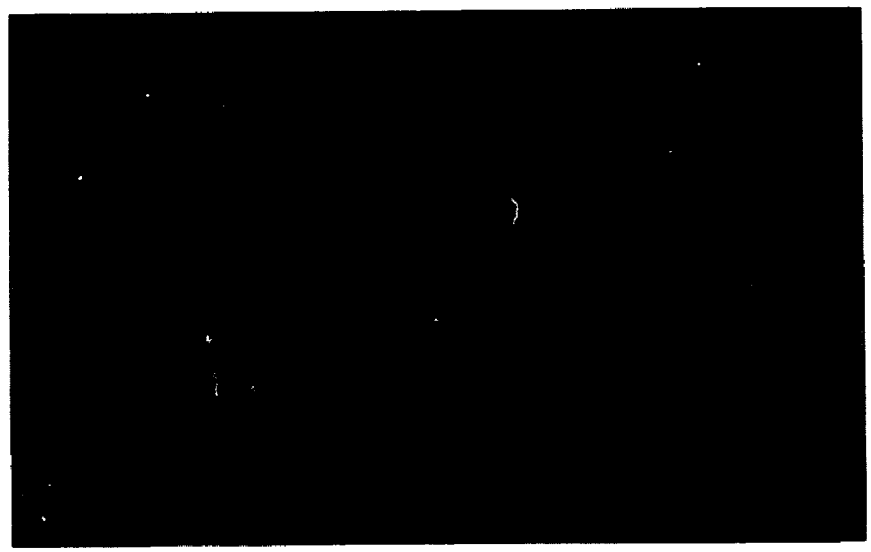

FIG. 13A is a light micrograph (about 15× magnification) of a drug-TFE/PPVE-polymer coated stent made according to this example and subjected to EtO sterilization at 67.7° C., before balloon expansion. FIG. 13B is a light micrograph (about 30× magnification) of the same stent after balloon expansion using a balloon as described in Example 8.

EXAMPLE 11

Figure 14:
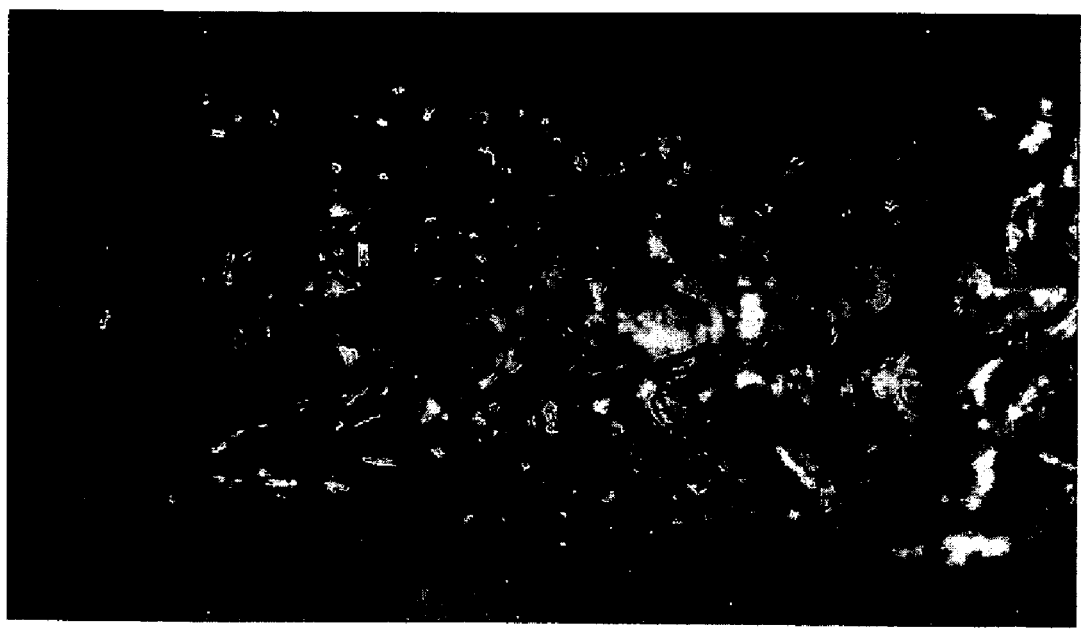
FIG. 14 is a light micrograph (about 10×) of a self-expanding stent-graft having a graft covering of the TFE/PMVE coating of the present invention.

Self-expanding Stent Having Interstices Coated with TFE/PMVE to form a Stent-graft More of the same TFE/PMVE copolymer, made as described by Example 1, was obtained in a 2 wt % solution of FC-75. The copolymer was added to a beaker for submersion of devices for coating. A self-expanding stent frame (4 cm length, 5 mm inner diameter) made from 0.152 mm diameter nitinol metal wire was also obtained. A thin wire was temporarily attached to one end of the stent as a handle and the stent frame was dipped into the solution, removed, and completely air-dried. The process was repeated until a polymer film coating extended between the nitinol wires, as shown by the finished device of FIG. 14 (about 10× magnification). The film initially contained void spaces, but these voids were filled as more layers were added. This process can be practiced to produce a polymer stent cover that is perforated (i.e., containing occasional void spaces or openings through the coating that extends between adjacent wires) or continuous (without openings).

EXAMPLE 12

Figure 15A:
FIGS. 15A and 15B are light micrographs (about 30×) of a TFE/PMVE polymer coated stent-graft, unsterilized, before and after balloon expansion.
Figure 15B:
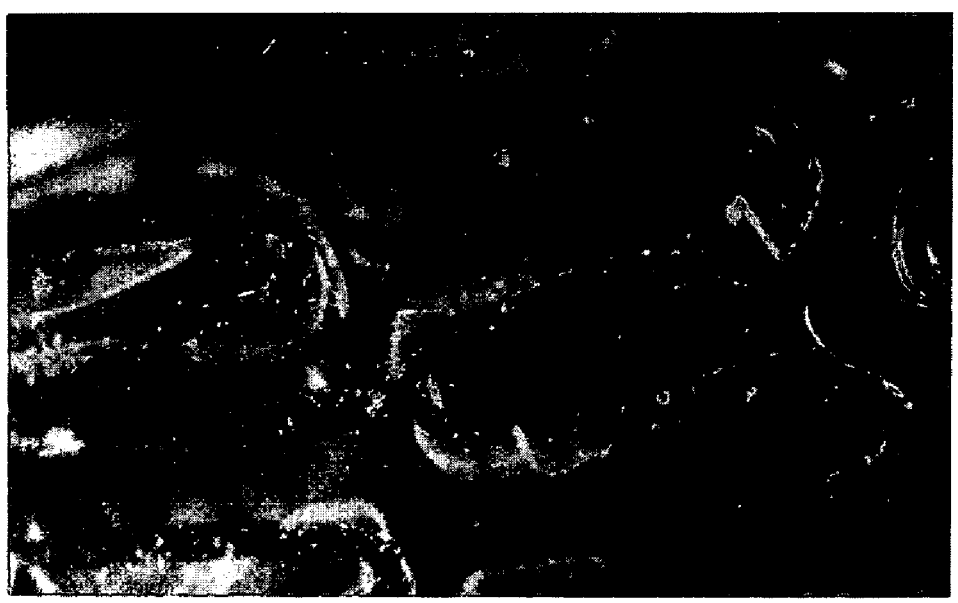

Balloon-expandable Stent Having Interstices Coated with TFE/PMVE to form a Stent-graft A sample of the same TFE/PMVE copolymer, made as described by Example 1, was prepared. The polymer was dissolved in FC-75 to obtain a 4 wt % solution. The working formulation was made by diluting 2.5 ml of the 4 wt % polymer solution with 5 ml of FC-75 and allowing the system to mix in a 15 ml plastic test tube, with periodic vortexing. Balloon expandable stents of the same type used in Example 5 were utilized. Each stent had a small wire temporarily looped through one end for handling during the subsequent dip-coating process. Once secured on the wire, the stent was dipped into the polymer solution, and placed in an air forced furnace for 5 minutes at 60° C. The dipping procedure was repeated until the void space between the stent elements is spanned with a continuous solid polymer coating. Once completed the stent-grafts were distended using a balloon as described in Example 8, and examined with a light microscope at magnification of up to 90×. FIG. 15A is a light micrograph (about 30× magnification) of a TFE/PMVE polymer coated stent-graft according to this example shown before expansion while FIG. 15B is a light micrograph (about 30× magnification) describing the same stent after balloon expansion using a balloon as described in Example 8. The finished, coated stent-graft has occasional perforations or openings through the graft covering where substantial amounts of deformation of adjacent stent elements occurred during expansion. FIG. 15B shows one such opening. The more opaque regions of the coating adjacent to some stent elements were determined to be internal void spaces or "pockets" in the coating that were formed during stent expansion. They do not represent openings through the coating. While this is believed to be an artifact of the type of balloon-expandable stent used, it remains noteworthy that a large majority of the stent-graft covering was not occupied by these openings. For some applications, a stent-graft with occasional openings may be desirable. The stent-graft shown in this figure was not subjected to EtO sterilization.

EXAMPLE 13

Balloon-expandable Stent Having Interstices Coated with TFE/PMVE to form a Stent-graft A sample of the same TFE/PMVE copolymer, made as described by Example 1, was prepared. The polymer was dissolved in FC-75 to obtain a 4 wt % solution. The working formulation was made by diluting 3 ml of the 4 wt % polymer solution with 3 ml of FC-75 and allowing the system to mix in a 15 ml plastic test tube, with periodic vortexing.

Figure 16A:
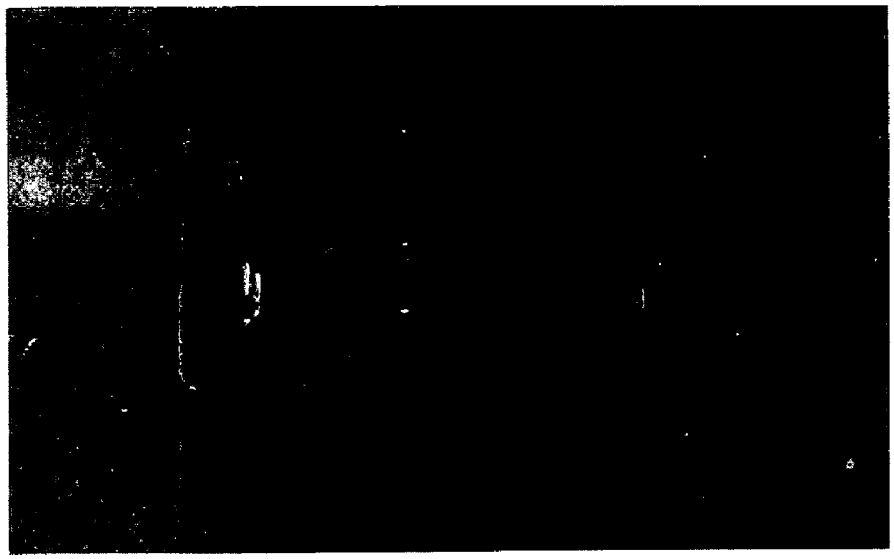
FIGS. 16A and 16B are light micrographs (about 30× and 15×, respectively) of TFE/PMVE polymer coated stent-graft, unsterilized, before and after balloon expansion.
Figure 16B:
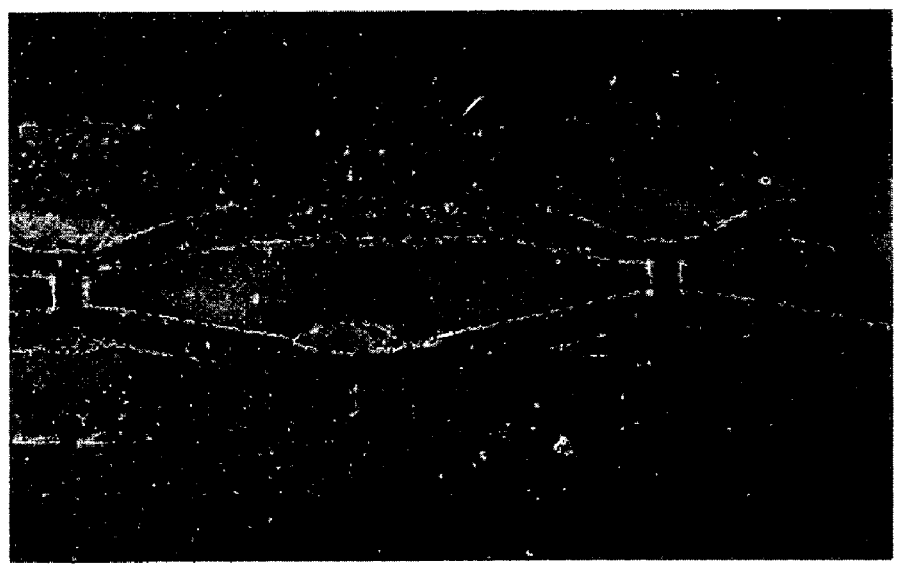

Stents made as taught by U.S. Pat. No. 4,733,665 to Palmaz, of 2 mm compacted diameter, were utilized. Each stent had a small wire temporarily looped through the end for handling during the subsequent dip-coating process. Once secured on the wire, the stent was dipped into the polymer solution, and then placed in a forced-air furnace set at 60° C. for a period of 5 minutes. This procedure was repeated to bring the total number of layers to 7. A Medi-tech 4 mm balloon (Boston Scientific, Medi-tech, Universal Product No. M001164180, Natick Mass.) was utilized to expand the stent-graft device. Some uneven distention of the device was noted and was believed to be related to the stent and not the polymer coating. FIG. 16A is a light micrograph (about 30× magnification) of this TFE/PMVE polymer coated stent-graft before expansion. FIG. 16B (about 15× magnification) shows the same stent-graft immediately after balloon expansion to 4 mm. The coating fully covers all of the stent interstices between adjacent stent elements, without any openings. The more opaque regions of the coating adjacent to some stent elements were determined to be internal void spaces or "pockets" in the coating that were formed during stent expansion. They do not represent openings through the coating. The stent-graft in this figure was not subjected to sterilization.

EXAMPLE 14

Stent-grafts Having an ePTFE Graft Covering, Coated with TFE/PMVE Containing Dexamethasone More of the same TFE/PMVE copolymer of Example 1 was obtained in a 2.5 wt % solution of FC-75. The drug formulation was a mixture of 2 ml of 2.5 wt % polymer, 8 ml of FC-75, and 120 mg of dexamethasone. This solution was well-mixed by shaking and then sprayed with a Badger standard set model 350 airbrush set at 220 KPa gauge air pressure. Nitinol wire-based, self-expanding, stents having a length of 4 cm, of the type used in Example 11, were obtained. Porous expanded PTFE material was used to cover both the internal and external stent frame surfaces. The inner ePTFE layer was constructed using an ePTFE tubing of about 25 microns thickness. The outer surface of this inner layer was provided with a thin coating of the TFE/PMVE copolymer for subsequent use as a thermally-activated adhesive to join the ePTFE and stent layers. The outer ePTFE layer was constructed by wrapping a 25 micron thick ePTFE tape about the outer stent surface. Both of these ePTFE materials were of about 25 micron average fibril length. These devices were placed into a convection oven set at 320° C. for five minutes to activate the adhesive. After removal from the oven and cooling to room temperature, the resulting 4 cm long stent-grafts were cut into three sections. The scalloped end sections were cut to into 1.5 cm lengths and the mid-section was cut into a 1 cm length. Each of these sections was mounted onto a mandrel, rotated by hand and spray coated. The airbrush was held approximately 3.8 cm from the graft surface. Spraying was continuously performed for 30 seconds, after which time the coated stent-graft on the mandrel was transferred to an oven set at 60° C. for 2 minutes. This spraying and heating process was repeated for up to 21 times. The devices were processed in three groups of 4 where, within each group, one stent-graft was for loading determination and the remaining 3 for release studies. The first group received 16 coats, the second 21, and the third 19 coats. Loading was periodically measured with the one stent-graft and the coating cycles adjusted to yield devices of comparable drug content.

Figure 17:
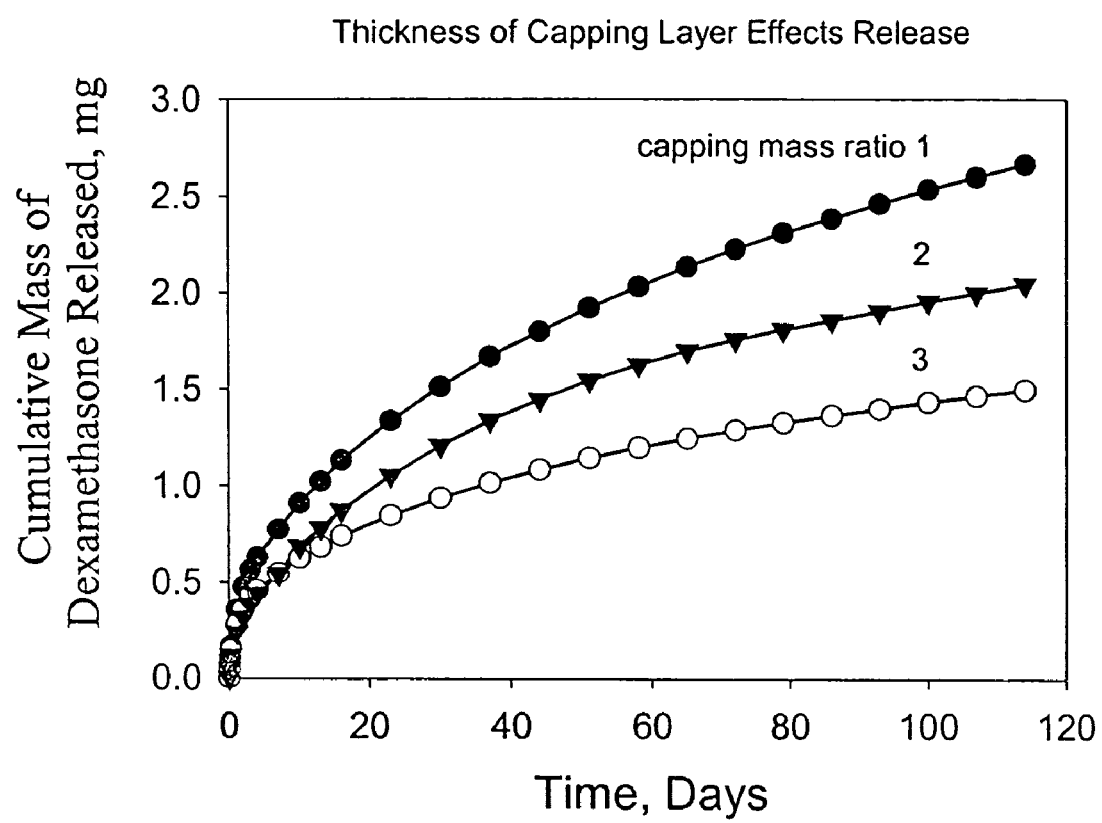
FIG. 17 is a graph of the cumulative mass of drug released as a function time and capping mass ratio for Example 14.

A capping layer was applied with a solution of polymer made from 2 ml of the 2.5 wt % in 8 ml of FC-75. This was sprayed in a similar manner as was the drug containing formulation. Three groups consisting of three different capping layers were created by applying 5, 10 and 15 capping coats to the appropriate stent-graft group. The capping mass ratios are shown in FIG. 17.

Samples were subjected to drug release studies, determination of total drug loading, and SEM analysis. For the release study, a sample of 1.5 cm length was placed into PBS and maintained at 37° C. Periodically, the fluid was collected, stored, and replaced with fresh PBS. Collected samples were assayed by UV spectrophotometric analysis to measure dexamethasone concentration. FIG. 17 shows the cumulative mass of dexamethasone released as a function of time. Loading determinations were performed by placing the sample in 5 ml of ethanol in a glass test tube over night at 60° C. After ethanol extraction, the solution was analyzed by a UV spectrophotometer for dexamethasone content. Loading values for the 1.5 cm long stent-grafts were estimated to be 13.3, 12.8 and 15 mg for the respective groups. The capping mass was determined through gross weight change and determined to be 3.0, 6.0, and 8.5 mg, respectively.

Additionally, stainless steel balloon expandable stents (about 1.5 mm unexpanded diameter) were obtained as described above. The stent was powder-coated with FEP. An ePTFE tube of about 1.4 mm diameter, 80 micron wall thickness and having a microstructure having an average fibril length of about 23 microns was obtained. This ePTFE tube was placed over a mandrel, the powder-coated stent placed over the tube, and another ePTFE tube of the same type was placed over the stent. The assembly was temporarily wrapped with an ePTFE film and placed in an oven set at 320° C. for five minutes. The ePTFE tubes were thereby bonded to the stent, thereby encapsulating it and forming a stent-graft. After removal from the oven and cooling to room temperature, the temporarily-applied ePTFE film was removed.

Next, three different spray formulations of TFE/PMVE copolymer made as described by Example 1 were utilized for coating the stent-graft. All formulations used polymer obtained in a 2.9 wt % solution of FC-75. The first drug formulation was a mixture of 1 ml of 2.9 wt % polymer, 5 ml of FC-75, and 25 mg of dexamethasone. This solution was well mixed by vortexing and sprayed with a Badger standard set model 350 airbrush set at 220 KPa gauge pressure. The stent-graft devices were placed onto mandrels and rotated by hand during the spraying process. The airbrush was held about 3.8 cm from the graft surface. In this manner only the abluminal surfaces of the devices were coated.

The second drug formulation was 1 ml of 2.9 wt % polymer, 5 ml of FC-75, 25 mg of dexamethasone, and 500 microliters of ethanol. The system was mixed by sonication for 15 min. and vortexed briefly. The third drug formulation was 1 ml of 2.9 wt % polymer, 5 ml of FC-75, 100 mg of dexamethasone, and 500 microliters of ethanol.

These coated expandable stent-grafts were balloon-expanded to a diameter of 4.5 mm and the polymer-drug coating was examined by SEM for integrity. The coating remained intact on the abluminal surface of the ePTFE after balloon expansion. Visual examination indicated that the coating appeared to change dimension with the diametrically expanding ePTFE in that it appeared to continue to be well-adhered to the ePTFE surface. Despite being forcibly distended with a balloon to a diameter three times larger than the compacted diameter, the coating remained well-adhered to the ePTFE surface of the stent-grafts.

EXAMPLE 15

Drug Delivery Effectiveness of Stent-graft

Self-expanding stent-grafts of 15 mm length, of the same type as described by Examples 11 and 14, were obtained. Polymer was obtained in a 4 wt % solution of FC-75. The working drug formulation was a mixture of 6 ml of 4 wt % polymer, 24 ml of FC-75, and 450 mg of dexamethasone (Pharmacia & UpJohn, Kalamazoo, Mich. USA). The formulation was made by weighing dexamethasone into a test tube, adding FC-75, vortexing vigorously to complete mixing, adding the polymer, and ensuring complete mixing with additional vortexing. This solution was sprayed with a Badger, standard set model 350, spray paint gun set at 220 KPa gauge air pressure to coat devices. Self-expanding stent-grafts of 15 mm length and 4, 4.5, and 5 mm diameters, of the type described in Example 14, were utilized. After the stent-grafts were mounted onto a mandrel, the mandrel was rotated by hand as the airbrush was moved back and forth across the stent-grafts. The airbrush was held at a constant distance of approximately 6 cm from the stent-graft surface. The coating was continuously sprayed for approximately 15 minutes, after which time the mandrel was transferred to an oven set at 60° C. for 2 minutes. A capping layer was applied with a solution of polymer made from 2 ml of the 4 wt % in 8 ml of FC-75. This was sprayed for about 2.5 minutes, in a similar manner as the drug containing formulation, to obtain a capping mass of about 1.7 mg.

Several samples at this stage of processing were retained for the determination of drug loading amount.

In order to provide the stent-grafts with a porous outer layer that would allow for tissue ingrowth, two layers of helically-wrapped ePTFE film were applied to the outer surface of the coated stent grafts. The film-wrapped stent-grafts were then heated to 200° C. for 3 minutes to bond layers. Ends were trimmed to allow the film to conform to the profile of the stent graft ends. Each stent-graft was diametrically compacted to an outer diameter of approximately 2.1 mm; this may be accomplished by various means known to those of skill in the art of self-expanding stents. The stent-grafts were constrained in the compacted state with a constraint wrap of more ePTFE film (not adhered), and were subjected to EtO sterilization with a total cycle time of 15 hours, including an EtO sterilization time of 1.3 hrs at 54.4° C.

Some of the stent-graft devices were mounted onto a 3 mm angioplasty balloon, distended to the point of breaking the ePTFE film constraint wrap, and then fully distended with appropriate balloon sizes consistent with stent-graft diameters.

The following tests were performed on the stent-grafts: total drug loading measurement, drug release characteristics, balloon deployment, and SEM analysis. Loading determinations were performed by placing each sample in 5 ml of ethanol in a glass test tube over night at 60° C. After ethanol extraction, the solution was analyzed by a UV spectrophotometer for dexamethasone content. For the drug release study, a small drop of alcohol was applied to the abluminal surface of the ePTFE stent-graft. The alcohol-wetted samples were immediately placed into PBS and maintained at 37° C. Periodically, the fluid was collected, stored, and replaced with fresh PBS. Collected samples were assayed by UV spectrophotometric analysis to measure dexamethasone concentration.

Total loading of dexamethasone was determined to be approximately 10 to 14 mg per stent-graft, and the polymer-drug layer was calculated to contain 63 wt % dexamethasone.

Figure 18:
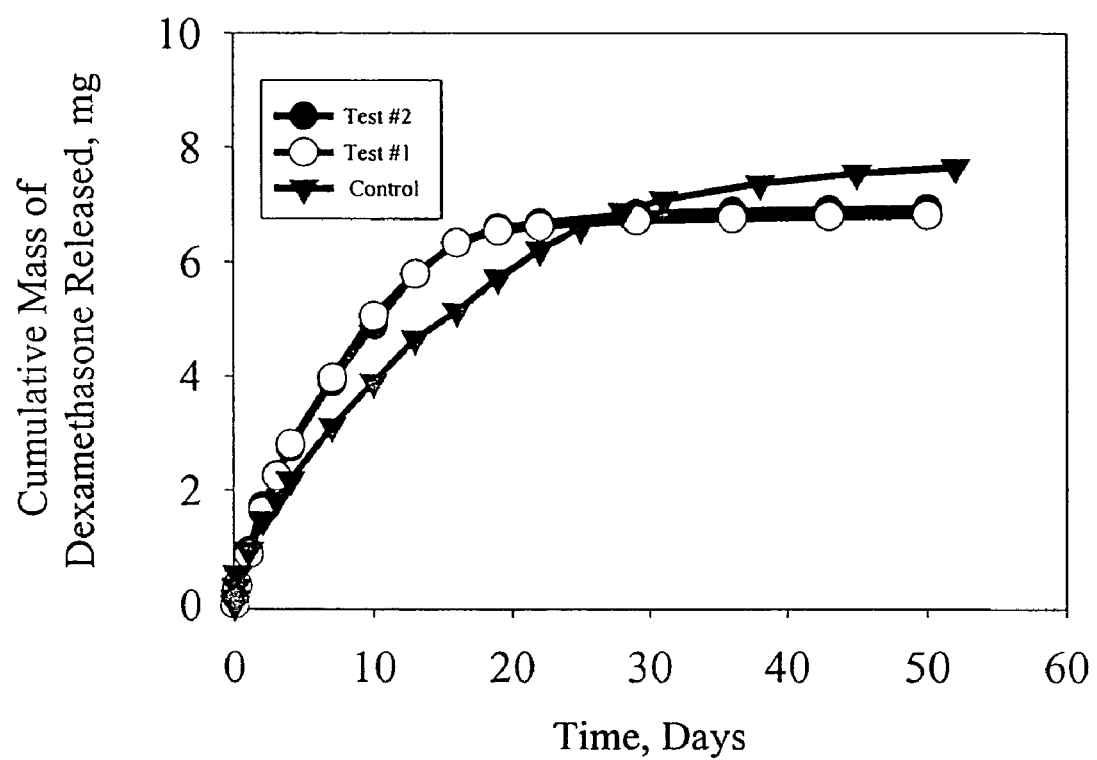
FIG. 18 is a graph of the cumulative mass of drug released as a function time for Example 15, where control device is filled triangles and test is open and filled circles.

FIG. 18 shows the cumulative mass of dexamethasone released as a function of time for the control device (filled triangles) and test devices (open and filled circles). The control device was not compacted, sterilized, nor balloon distended; the test devices were subjected to all of these steps. The absence of spikes in the curves for the test grafts indicates the absence of cracking of the coating. Had the coating cracked, the drug elution curve would have demonstrated discontinuities associated with non-uniform delivery. The two test stent-grafts show remarkable consistency in the release of dexamethasone after having been subjected to the physically challenging thermal and mechanical stresses. Furthermore, the test stent-grafts have retained the basic release characteristics of the control device with minimum deviation. From visual inspection of the curves in FIG. 18, it is evident that the curves are all very similar. From a pharmacokinetic standpoint two systems are generally equivalent if they deliver the same total quantity of drug and at the same rate (duration of delivery). The total drug delivered is take at the plateau regions of FIG. 18, and is determined to be 7.66 mg for control, and 6.935 mg and 6.811 mg for test samples. On a percentage basis the test samples are within 11% of the control. This is remarkable in that the total drug loading for the devices is 10 mg, but only a consistent fraction of this is released as some remains trapped within the matrix. The test samples that underwent mechanical and thermal stress did not provide a total dose meaningfully different than the control.

These results attest to the surprising robustness of the drug delivery matrix under the conditions of high drug loading, severe mechanical and thermal stress, including balloon distention. These findings are even more significant inasmuch as the amount of drug loading was so high that it exceeded typical therapeutic levels.

EXAMPLE 16

Balloon-expandable Stent Having Interstices Coated with TFE/PPVE to form a Stent-graft A sample of TFE/PPVE copolymer described by Example 9 was prepared. The polymer was dissolved in FC-75 to obtain a 20 wt % solution. The working formulation was made by diluting 2 ml of the 20 wt % polymer solution with 8 ml of FC-75 and allowing the system to mix in a 15 ml plastic test tube, with periodic vortexing.

Balloon expandable stents of the same type used in Example 5 were utilized. Each stent had a small wire temporarily looped through one end for handling during the subsequent dip-coating process. Once secured on the wire, the stent was dipped into the polymer solution, and placed in an air forced furnace for 5 minutes at 60° C. The dipping procedure was repeated to bring the total number of layers to 6. A portion of the stent-grafts were expanded before sterilization with a balloon as described in Example 8, and examined with the use of a light microscope. Additional coated stent-grafts underwent EtO sterilization with a total cycle time of 15 hours, including an EtO sterilization time of 1.3 hours at 67.7° C. After sterilization the stent-graft was distended using a balloon as described in Example 8, and examined with a light microscope at magnification of up to 90×. As the occlusive stent-graft expands, openings through the coating are created, the size, location, and morphology of which are related to the metal stent design. The implications of this are that the metal stent design can be utilized to produce a stent-graft having openings through the coating when expanded of predetermined size, and the metal stent design could be made to not facilitate the formation of openings resulting in an occlusive stent-graft post expansion.

Figure 19A:
FIGS. 19A and 19B are light micrographs (about 15× and 20×, respectively) of an EtO sterilized, TFE/PPVE-polymer coated stent-graft before and after balloon expansion.
Figure 19B:
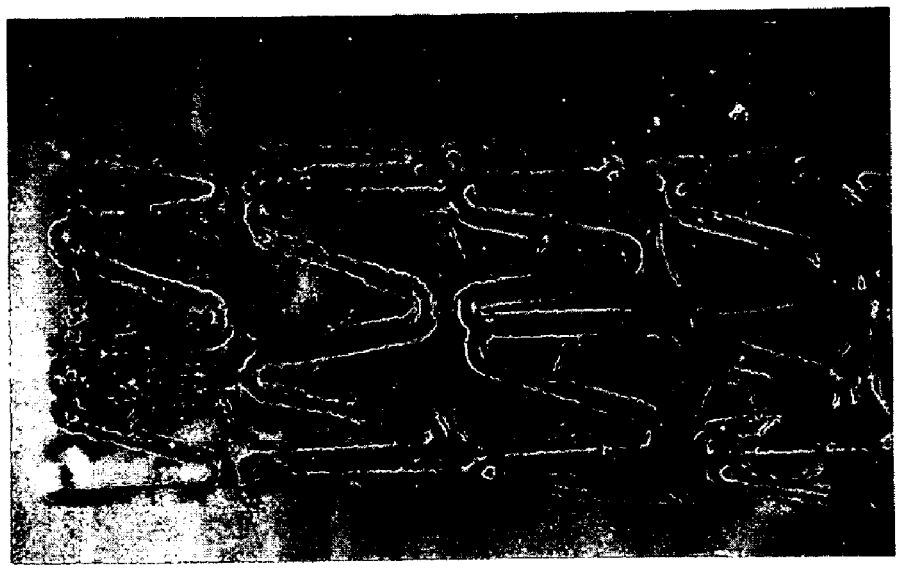

FIG. 19A is a light micrograph (about 15× magnification) of the TFE/PPVE-polymer coated stent-graft of this example shown before expansion, while FIG. 19B (about 20× magnification) shows the same stent-graft after balloon expansion using a balloon as described in Example 8. Stent-grafts in this figure were EtO sterilized as described for previous examples.

EXAMPLE 17

TFE/PPVE Stent-graft with TFE/PMVE Drug Layer

A sample of the TFE/PPVE copolymer described by Example 9 was prepared. The polymer was dissolved in FC-75 to obtain a 20 wt % solution. The working formulation was made by diluting 2 ml of the 20 wt % polymer solution with 8 ml of FC-75 and allowing the system to mix in a 15 ml plastic test tube, with periodic vortexing.

A TFE/PMVE copolymer formulation containing the drug dexamethasone was also prepared. The TFE/PMVE copolymer was dissolved in FC-75 to obtain a 4 wt % solution. One hundred and twenty mg of dexamethasone as a powder was weighed into a 15 ml plastic test tube, 6 ml of FC-75 was added, and the system was mixed vigorously to ensure complete mixing. Two grams of the 4 wt % TFE/PMVE polymer solution was added and the mixture was vortexed. This formulation is 60 wt % dexamethasone on a total solids basis.

Balloon expandable stents of the same type used in Example 5 were utilized. Each stent had a small wire temporarily looped through one end for handling during the subsequent dip-coating process. Once secured on the wire, the stent was dipped into the TFE/PPVE polymer solution, and placed in an air forced furnace for 5 minutes at 60° C. The dipping procedure was repeated to bring the total number of layers to 6. An additional layer containing the drug dexamethasone in TFE/PMVE was applied to the abluminal stent-graft surface. This was sprayed onto the stent-graft using a Badger, standard set model 350 airbrush set at 220 KPa gauge air pressure. An end portion of the stent-graft was mounted onto a mandrel and then the mandrel was rotated by hand as the airbrush was moved back and forth across the stent-graft surface. The coating was continuously sprayed for approximately 15 seconds, after which time the mandrel was transferred to an oven set at 60° C. for 2 minutes.

A portion of the stent-grafts were expanded with a balloon as described in Example 8, and examined with the use of a light microscope. A coated stent-graft underwent EtO sterilization with a total cycle time of 15 hours, including an EtO sterilization time of 1.3 hours at 67.7° C. After sterilization the stent-graft was distended using a 3.5 mm PTFE balloon and examined with a light microscope at magnification of up to 90×. The drug-containing layer of TFE/PMVE did not separate from the base material of TFE/PPVE; and appeared to be tough, well adherent, and without evidence of cracking, demonstrating a high degree of stability. It is apparent that different copolymers of the PAVE family can be easily integrated into a single device construct, with or without additives.

Figure 20A:
FIGS. 20A and 20B are light micrographs (about 25× and 30×, respectively) of a TFE/PPVE-polymer coated stent-graft including a TFE/PMVE drug-containing layer, shown before and after expansion.
Figure 20B:
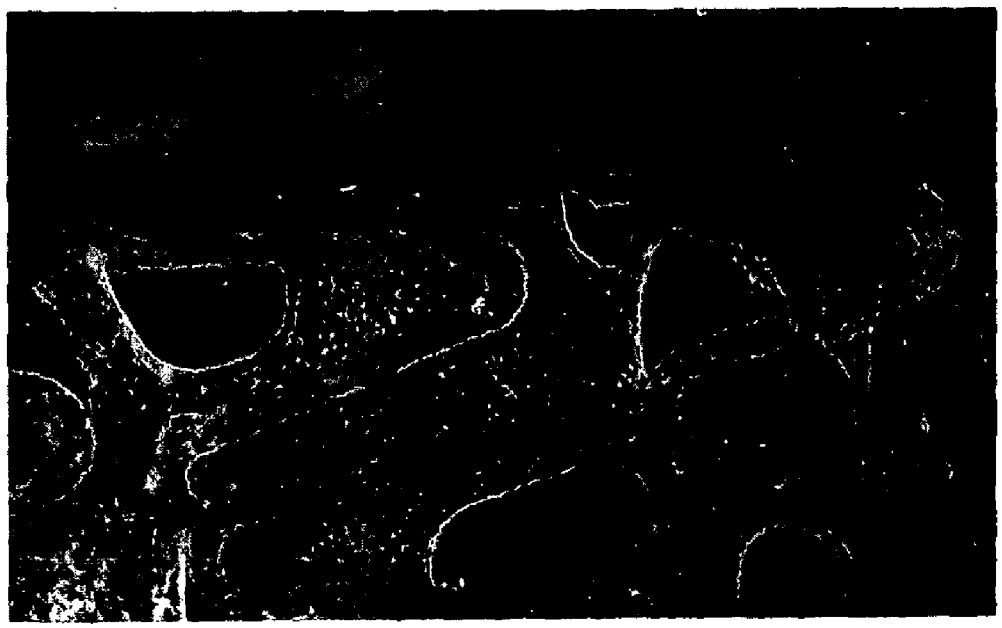

FIG. 20A is a light micrograph (about 25× magnification) of the TFE/PPVE-polymer coated stent-graft including the TFE/PMVE drug-containing layer, shown before expansion. FIG. 20B (about 30× magnification) shows the same stent-graft following expansion with a balloon of the type described in Example 8. While the covering shows occasional periodic and well-defined perforations or openings through the expanded stent-graft, the large majority of the stent-graft is unperforated. The stent-graft shown in these figures was not subjected to EtO sterilization.

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

The invention claimed is:

1. An implantable device comprising a device having expandable endoluminal elements in adjacent relationship with an open interstice between adjacent expandable endoluminal elements, said expandable endoluminal elements provided with a covering over at least one open interstice rendering it no longer open, wherein at least a portion of said covering and at least a portion of said endoluminal elements are provided with a coating comprising a thermoplastic copolymer of tetrafluoroethylene and perfluoroalkylvinylether.

2. An implantable device according to claim 1 wherein said coating contains a therapeutic agent capable of eluting from the coating over time following implantation in a body conduit.

3. An implantable device according to claim 1 wherein said device is a stent-graft having a small, compacted form expandable to a larger form.

4. An implantable device according to claim 3 wherein said coating contains a therapeutic agent that elutes from the coating over time following implantation in a body conduit.

5. An implantable device according to claim 3 wherein the larger expanded form of said stent-graft has an outside diameter 50 percent larger than said small, compacted form.

6. An implantable device according to claim 3 wherein said covering comprises polyethylene terephthalate.

7. An implantable device according to claim 3 wherein said covering comprises polytetrafluoroethylene.

8. An implantable device according to claim 7 wherein said coating comprises a copolymer of tetrafluoroethylene and perfluoromethylvinylether.

9. An implantable device according to claim 7 wherein said coating contains a therapeutic agent that elutes from the coating over time following implantation in a body conduit.

10. An implantable device according to claim 1 wherein said coating comprises a copolymer of tetrafluoroethylene and perfluoromethylvinylether.

11. An implantable device according to claim 1 wherein said coating comprises a copolymer of tetrafluoroethylene and perfluoroethylvinylether.

12. An implantable device according to claim 1 wherein said coating comprises a copolymer of tetrafluoroethylene and perfluoropropylvinylether.

13. An implantable device according to claim 1 wherein the copolymer is an amorphous thermoplastic.

* * * * *